(12) United States Patent
Wakai et al.

(10) Patent No.: US 10,155,316 B2
(45) Date of Patent: Dec. 18, 2018

(54) MANIPULATOR-CALIBRATING METHOD, MANIPULATOR, AND MANIPULATOR SYSTEM

(71) Applicant: OLYMPUS CORPORATION, Tokyo (JP)

(72) Inventors: Hiroshi Wakai, Tokyo (JP); Masatoshi Iida, Tokyo (JP); Naoya Hatakeyama, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 152 days.

(21) Appl. No.: 15/246,677

(22) Filed: Aug. 25, 2016

(65) Prior Publication Data

US 2016/0361819 A1 Dec. 15, 2016

Related U.S. Application Data

(63) Continuation of application No. PCT/JP2015/054967, filed on Feb. 23, 2015.

(30) Foreign Application Priority Data

Feb. 28, 2014 (JP) ................................. 2014-039369

(51) Int. Cl.
*G06F 19/00* (2018.01)
*B25J 9/16* (2006.01)
(Continued)

(52) U.S. Cl.
CPC ......... *B25J 9/1692* (2013.01); *A61B 1/00006* (2013.01); *A61B 1/00009* (2013.01); (Continued)

(58) Field of Classification Search
CPC ... B25J 9/1692; B25J 13/085; G02B 23/2476; A61B 34/37; A61B 34/71; (Continued)

(56) References Cited

U.S. PATENT DOCUMENTS

| 8,412,378 B2 | 4/2013 | Abdallah et al. |
| 8,812,257 B2 * | 8/2014 | Kohler .................. B25J 9/1692 |
| | | 702/94 |

(Continued)

FOREIGN PATENT DOCUMENTS

| EP | 2462858 A1 | 6/2012 |
| JP | H10-174686 A | 6/1998 |

(Continued)

OTHER PUBLICATIONS

Japanese Office Action dated Jun. 6, 2017 in Japanese Patent Application No. 2014-039369.

(Continued)

*Primary Examiner* — Ronnie M Mancho
(74) *Attorney, Agent, or Firm* — Scully, Scott, Murphy & Presser, P.C.

(57) ABSTRACT

A method of calibrating a manipulator including a joint portion, a drive unit that generates a driving force for driving the joint portion, and a driving force transmission member that is inserted into a tubular member and transmits the driving force generated from the drive unit to the joint portion includes: an arrangement step of arranging the manipulator in a usable state; a load-measuring step of issuing an operation command based on a predetermined calibrating drive pattern to the drive unit and measuring a load generated in the manipulator at that time; and a control parameter-setting step of setting a main-driving control parameter based on the load measured in the load-measuring step.

20 Claims, 22 Drawing Sheets

(51) Int. Cl.
*A61B 1/00* (2006.01)
*G02B 23/24* (2006.01)
*A61B 34/00* (2016.01)
*A61B 34/37* (2016.01)
*B25J 13/08* (2006.01)
*A61B 17/00* (2006.01)
*A61B 34/30* (2016.01)
*A61B 34/20* (2016.01)
*A61B 90/00* (2016.01)

(52) U.S. Cl.
CPC ...... *A61B 1/00057* (2013.01); *A61B 1/00087* (2013.01); *A61B 1/00133* (2013.01); *A61B 1/00149* (2013.01); *A61B 34/37* (2016.02); *A61B 34/71* (2016.02); *B25J 13/085* (2013.01); *G02B 23/2476* (2013.01); *A61B 2017/00725* (2013.01); *A61B 2034/2065* (2016.02); *A61B 2034/301* (2016.02); *A61B 2090/064* (2016.02); *G05B 2219/39024* (2013.01)

(58) Field of Classification Search
CPC ............ A61B 1/00006; A61B 1/00009; A61B 1/00057; A61B 1/00087; A61B 1/00133; A61B 1/00149
USPC .................................................. 700/245, 248
See application file for complete search history.

(56) References Cited

U.S. PATENT DOCUMENTS

| | | | |
|---|---|---|---|
| 9,392,931 B2* | 7/2016 | Urban | A61B 34/30 |
| 9,469,034 B2* | 10/2016 | Diolaiti | A61B 1/00087 |
| 9,492,240 B2* | 11/2016 | Itkowitz | A61B 34/37 |
| 9,498,291 B2* | 11/2016 | Balaji | A61B 34/30 |
| 9,526,587 B2* | 12/2016 | Zhao | A61B 34/30 |
| 9,549,663 B2* | 1/2017 | Larkin | A61B 1/00087 |
| 9,603,667 B2* | 3/2017 | Yang | A61B 34/76 |
| 9,603,672 B2* | 3/2017 | Shellenberger | A61B 34/30 |
| 9,775,681 B2* | 10/2017 | Quaid | A61B 34/30 |
| 9,788,909 B2* | 10/2017 | Larkin | A61B 34/20 |
| 9,814,527 B2* | 11/2017 | Rogers | A61B 1/00149 |
| 9,855,101 B2* | 1/2018 | Wenderow | A61B 34/37 |
| 9,855,662 B2* | 1/2018 | Ruiz Morales | B25J 13/085 |
| 9,867,669 B2* | 1/2018 | Zhao | A61B 34/20 |
| 9,895,813 B2* | 2/2018 | Blumenkranz | B25J 13/085 |
| 2004/0138530 A1 | 7/2004 | Kawai et al. | |
| 2008/0103491 A1 | 5/2008 | Omori et al. | |
| 2008/0114494 A1 | 5/2008 | Nixon | |
| 2009/0012365 A1 | 1/2009 | Ueno et al. | |
| 2009/0112060 A1 | 4/2009 | Sugiyama et al. | |
| 2010/0082041 A1 | 4/2010 | Prisco | |

FOREIGN PATENT DOCUMENTS

| | | |
|---|---|---|
| JP | 2001-145638 A | 5/2001 |
| JP | 2002-059380 A | 2/2002 |
| JP | 2004-041538 A | 2/2004 |
| JP | 2006-314775 A | 11/2006 |
| JP | 2007-029167 A | 2/2007 |
| JP | 2008-104854 A | 5/2008 |
| JP | 2009-101077 A | 5/2009 |
| JP | 2010-046384 A | 3/2010 |
| JP | 2012-504016 A | 2/2012 |
| WO | WO 2011/108161 A1 | 9/2011 |

OTHER PUBLICATIONS

International Search Report dated Apr. 21, 2015 issued in PCT/JP2015/054967.
Extended Supplementary European Search Report dated Mar. 19, 2018 in European Patent Application No. 15 75 5013.8.

* cited by examiner

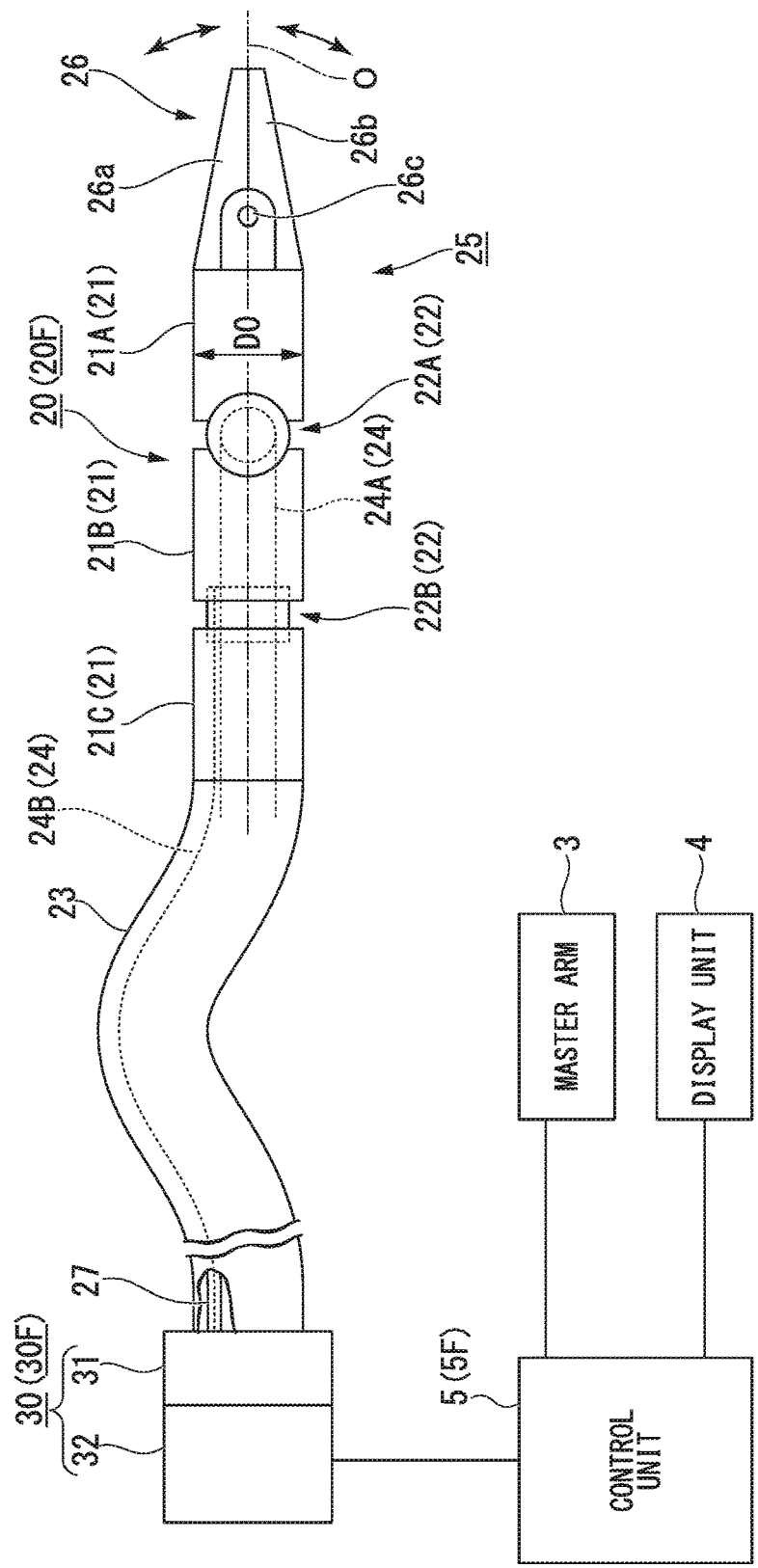

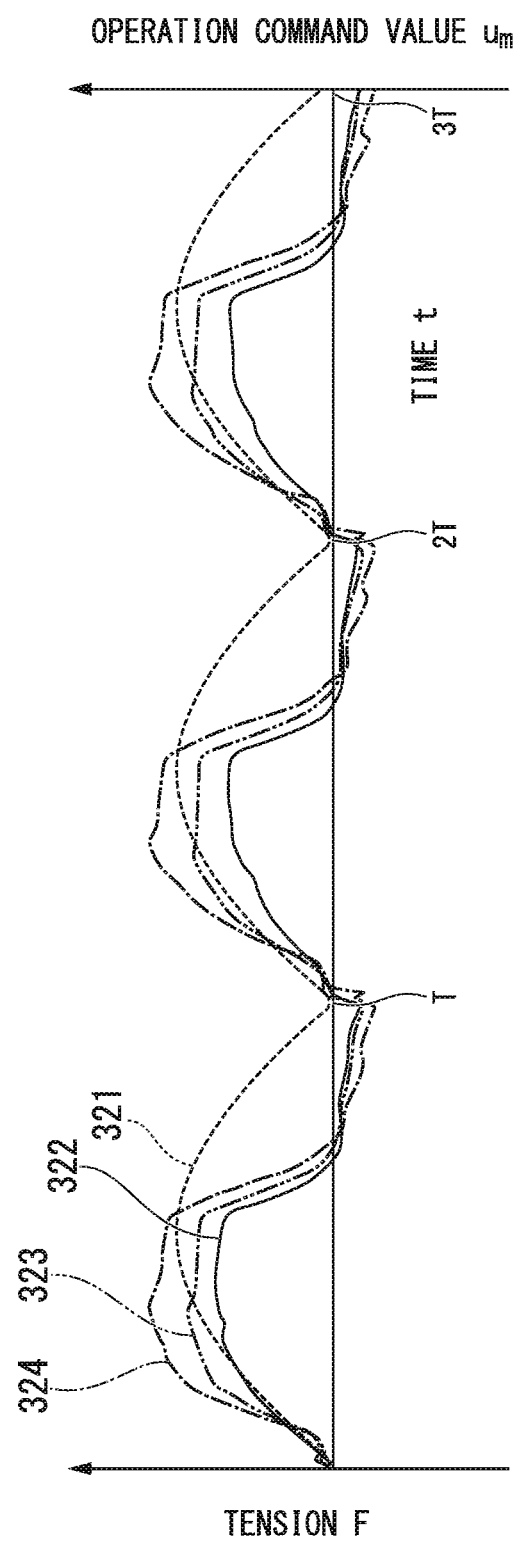

MANIPULATOR-CALIBRATING METHOD, MANIPULATOR, AND MANIPULATOR SYSTEM

This application is a continuation application based on a PCT International Application No. PCT/JP2015/054967, filed on Feb. 23, 2015, whose priority is claimed on Japanese Patent Application No. 2014-039369, filed on Feb. 28, 2014. The contents of both the PCT International Application and the Japanese Patent Application are incorporated herein by reference.

BACKGROUND OF THE INVENTION

Field of the Invention

The present invention relates to a manipulator system-calibrating method, a manipulator, and a manipulator system.

Description of Related Art

Conventionally, a manipulator system in which a distal end portion of a manipulator is provided with a movable portion and the movable portion is manipulated by transmitting a driving force of a motor to the movable portion via a wire is known. In such a manipulator, calibration is carried out such that the movable portion operates to accurately follow a manipulation input.

For example, a treatment tool described in U.S. Patent Application, Publication No. 2008/0114494 includes a pair of jaws, which is opened and closed by driving a wire, at a distal end portion thereof to grasp a treatment target and a proximal end thereof is provided with a motor pulling the wire and a master manipulation unit supplying a manipulation input to the motor.

In such a treatment tool, it has been proposed that calibration is carried out by moving the first jaw to the second jaw and measuring a position of the second jaw relative to the first jaw and an amount of torque generated at that time.

SUMMARY OF THE INVENTION

According to a first aspect of the present invention, a manipulator-calibrating method according of calibrating a manipulator, that includes a joint portion, a drive unit that generates a driving force for driving the joint portion, and a driving force transmission member that is inserted into a tubular member and provided to transmit the driving force generated from the drive unit to the joint portion, includes: an arrangement step of arranging the manipulator in an usable state; a load-measuring step of issuing an operation command based on a predetermined calibrating drive pattern to the drive unit and measuring a load generated in the manipulator at that time; and a control parameter-setting step of setting a main-driving control parameter based on the load measured in the load-measuring step.

BRIEF DESCRIPTION OF DRAWINGS

FIG. 4 is a diagram schematically showing a system configuration of the manipulator according to the first embodiment of the present invention.

FIG. 13 is a graph showing an example of a change of a tension due to a difference in load condition of the manipulator according to the first embodiment of the present invention.

DETAILED DESCRIPTION OF THE INVENTION

Figure 1:
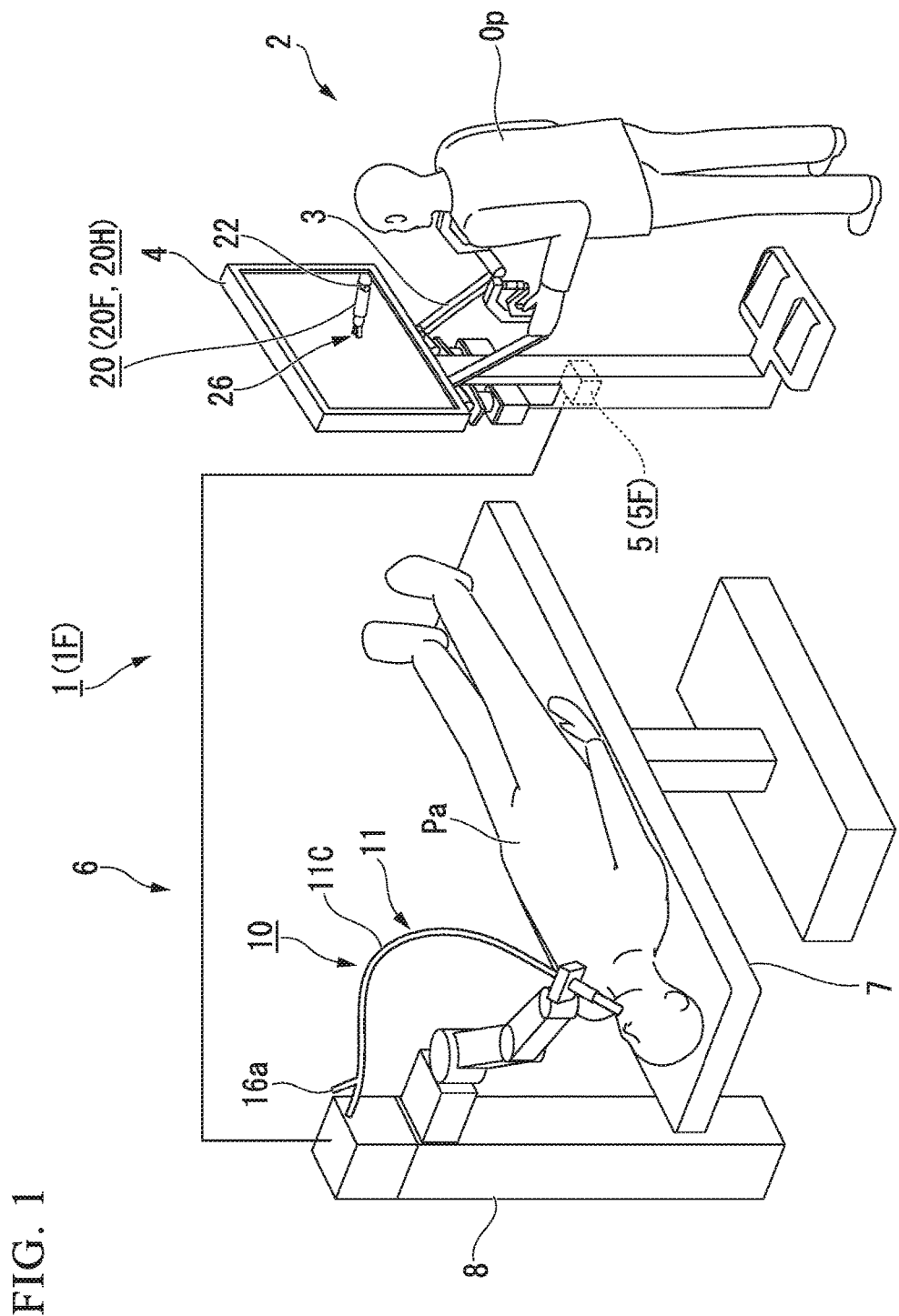
FIG. 1 is a schematic perspective view showing an entire configuration of a manipulator system according to a first embodiment of the present invention.

Hereinafter, embodiments of the present invention will be described with reference to the accompanying drawings. In the drawings, identical or corresponding members in different embodiments will be referenced by the same reference signs and description thereof will not be repeated.

First Embodiment

A manipulator system according to a first embodiment of the present invention will be described below.

Figure 2:
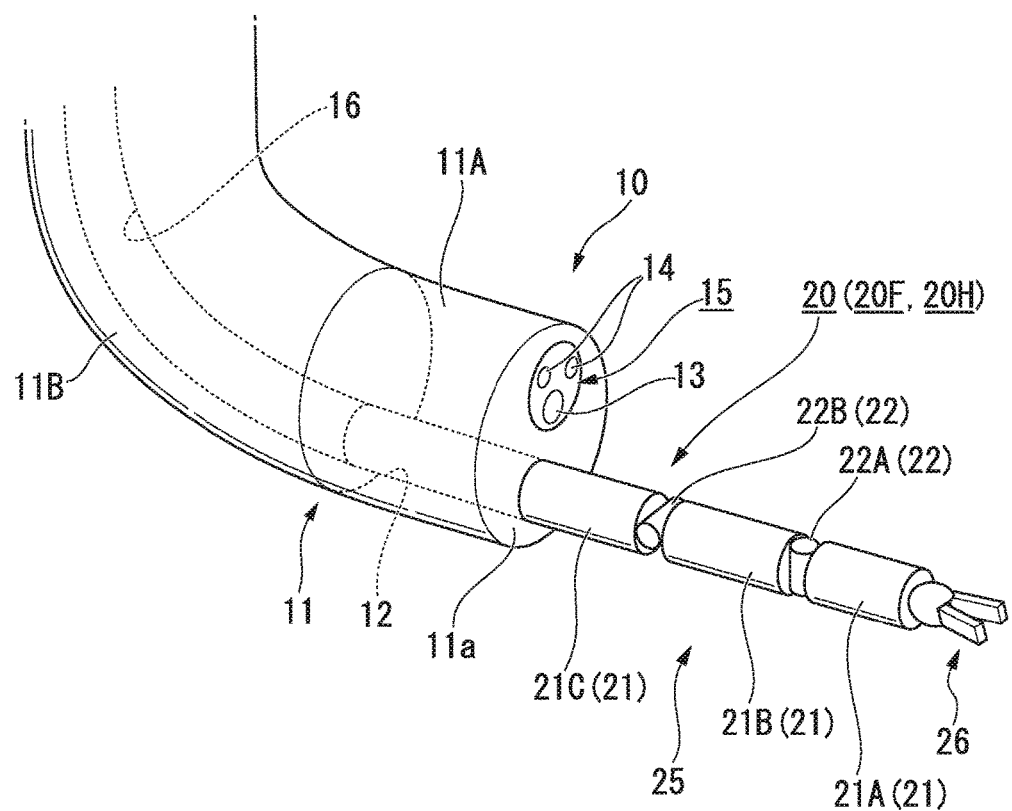
FIG. 2 is a schematic perspective view showing the joint portion-restricting member and the manipulator according to the first embodiment of the present invention.
Figure 3A:
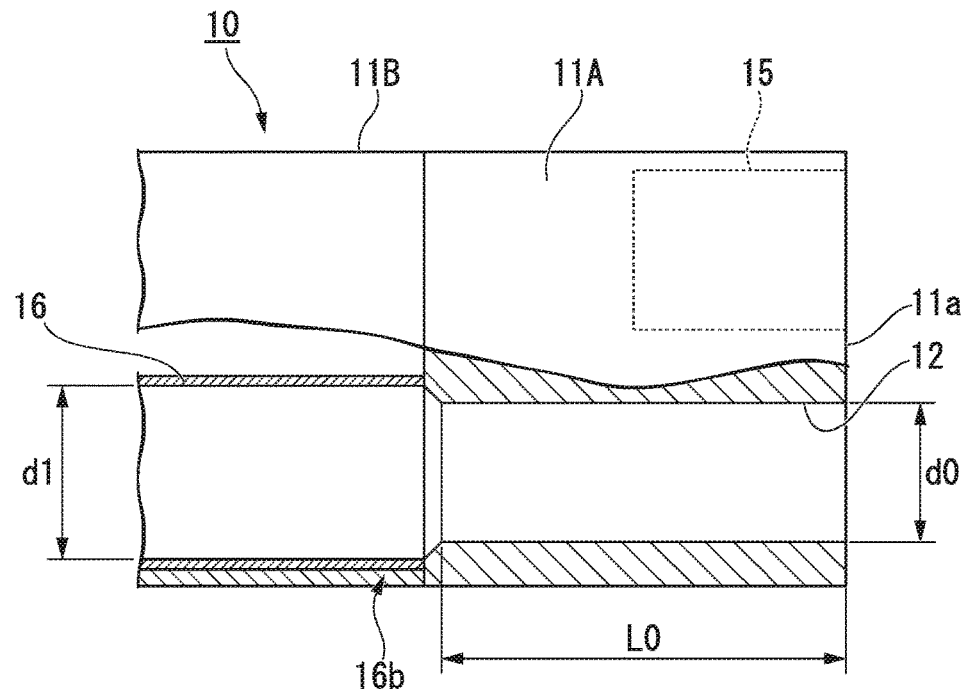
FIG. 3A is a partial cross-sectional view showing the joint portion-restricting member of the manipulator according to the first embodiment of the present invention.
Figure 3B:
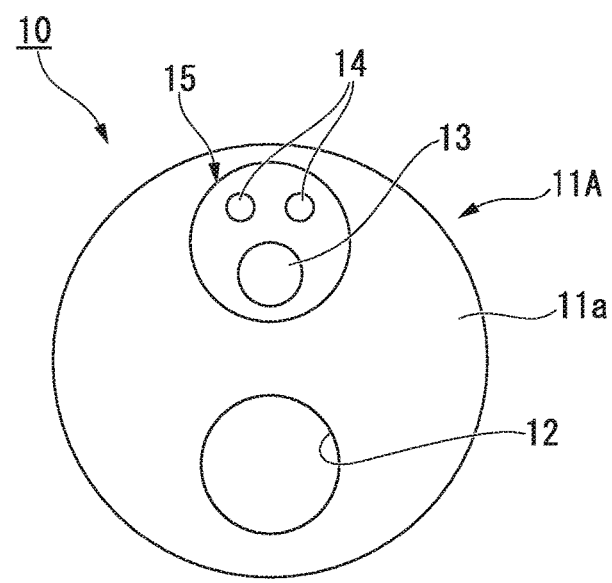
FIG. 3B is a right side view of the partial cross-sectional view showing the joint portion-restricting member of the manipulator according to the first embodiment of the present invention.
Figure 5:
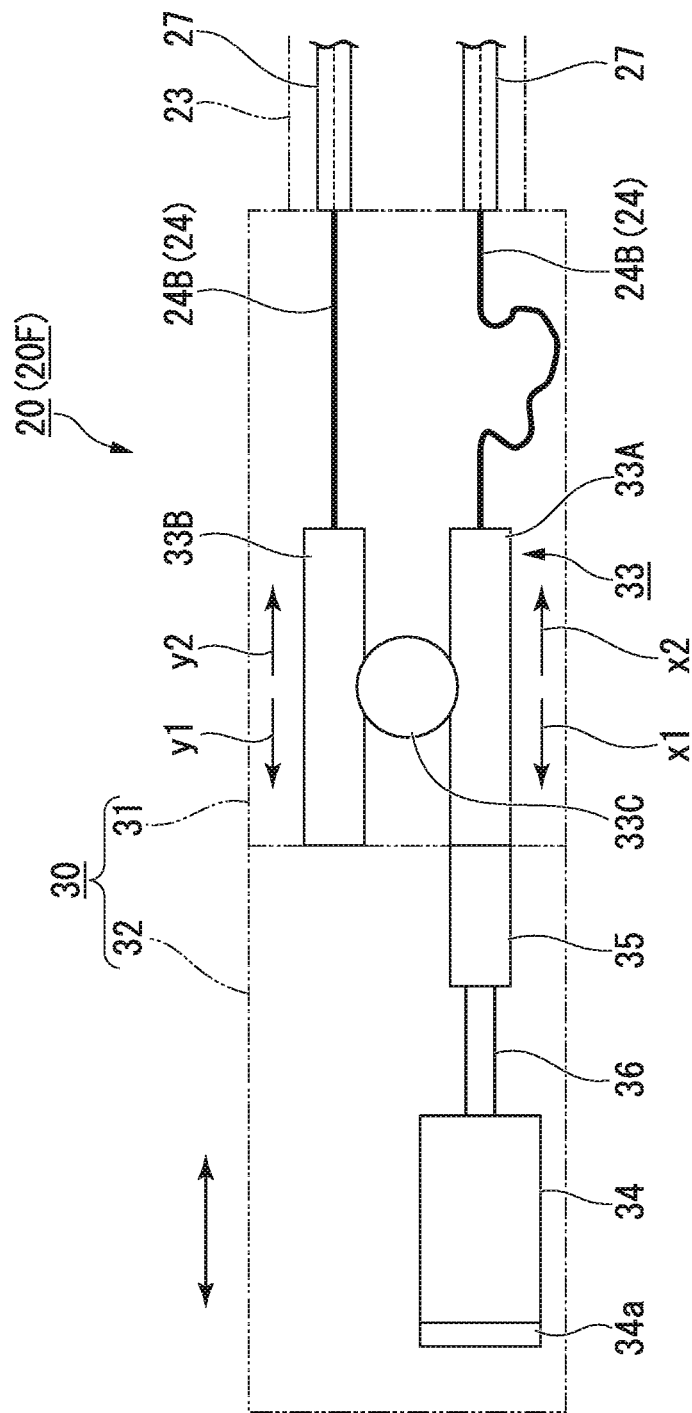
FIG. 5 is a configuration diagram schematically showing an example of a drive unit of the manipulator according to the first embodiment of the present invention.
Figure 6:
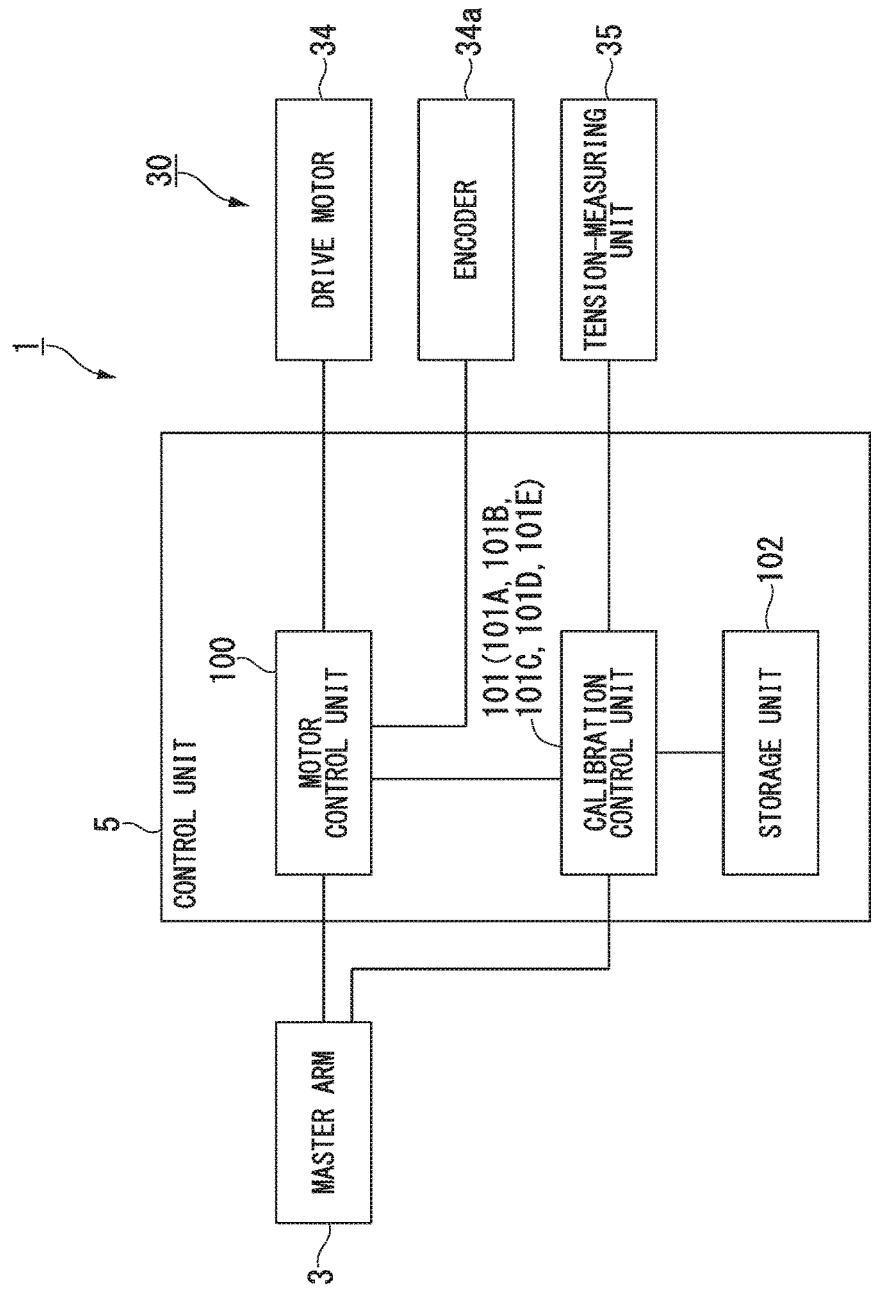
FIG. 6 is a functional block diagram showing a functional configuration of a control unit of the manipulator according to the first embodiment of the present invention.

FIG. 1 is a schematic perspective view showing an entire configuration of a manipulator system according to a first embodiment of the present invention. FIG. 2 is a schematic perspective view showing the joint portion-restricting member and the manipulator according to the first embodiment of the present invention. FIG. 3A is a partial cross-sectional view showing the joint portion-restricting member of the manipulator according to the first embodiment of the present invention. FIG. 3B is a right side view of FIG. 3A. FIG. 4 is a diagram schematically showing a system configuration of the manipulator according to the first embodiment of the present invention. FIG. 5 is a configuration diagram schematically showing an example of a drive unit of the manipulator according to the first embodiment of the present invention. FIG. 6 is a functional block diagram showing a functional configuration of a control unit of the manipulator according to the first embodiment of the present invention.

The drawings are schematic diagrams and thus sizes or shapes are appropriately modified (the same is true of the subsequent drawings).

As shown in FIG. 1, a manipulator system 1 according to this embodiment is a so-called master-slave system including a master manipulator 2 which is manipulated by an operator Op and a slave manipulator 6 which is provided with a treatment endoscope device 10.

The master manipulator 2 includes a master arm 3 to which a manipulation input is input by the operator Op, a display unit 4 that displays an image or the like which is captured using the treatment endoscope device 10, and a control unit 6 that generates an operation command for causing the slave manipulator 6 to operate based on the operation of the master arm 3.

In this embodiment, the master arm 3 is a manipulation unit that causes the portions of the slave manipulator 6 including a medical device 20 to be described later to operate. Although details are not shown, the master manipulator 2 includes a pair of master arms 3 corresponding to a right hand and a left hand of an operator Op.

The master arm 3 has a joint structure for causing a manipulator having a joint with at least one degree of freedom to operate, such as a bending portion 11B of the treatment endoscope device 10 and the joint portion 22 of a medical device 20 to be described later.

An end of the master arm 3 which is located at the operator Op side is provided with a gripping manipulation unit (not shown) for causing a grasping portion 26 (to be described later) of the medical device 20.

Although not particularly shown, the master arm 3 is provided with a manipulation unit for allowing the operator Op to instruct start of a calibration operation. For example, a push button manipulation unit or a foot switch manipulation unit may be employed as the manipulation unit. It is assumed that the push button manipulation unit for starting a calibration operation is disposed within a reachable range of a finger of an operator Op gripping the master arm 3.

The display unit 4 is a device that displays an image of a treatment target part captured by an observation unit 15 (to be described later) attached to the treatment endoscope device 10, a manipulation screen required for manipulation, information from the control unit 5, and the like. The display unit 4 displays the medical device 20 along with the treatment target part.

The slave manipulator 6 includes a surgical table 7 on which a patient Pa is placed, a multi-joint robot 8 that is disposed around the surgical table 7, and a medical device 20.

The treatment endoscope device 10 is held by the multi-joint robot 8. The medical device 20 can be inserted into the treatment endoscope device 10.

The multi-joint robot 8, the treatment endoscope device 10, and the medical device 20 operate in accordance with an operation command issued from the master manipulator 2.

In the manipulator system according to the present invention, the multi-joint robot is not essential but, for example, a configuration in which an assistant who is not shown holds the treatment endoscope device 10 may be employed.

As shown in FIG. 2, the treatment endoscope device 10 includes an outer sheath 11 which is a long member which is inserted into the body of a patient Pa.

The outer sheath 11 includes a flexible tubular insertion portion 11C (see FIG. 1), a known bending portion 11B having, for example, joint rings or curving pieces, and a cylindrical distal end portion 11A (joint portion-restricting member) which is formed of a hard material in this order from the proximal end to the distal end.

The bending portion 11B can change the direction of the distal end portion 11A by curving in response to a manipulation input to the master arm 3. A known configuration in which a driving wire which is inserted into the inner circumferential surface of the joint rings or the curving pieces and fixed to the distal end portion 11A is inserted into the insertion portion 11C and is pulled by the drive motor or the like at the proximal end side can be employed as a mechanism for curving the bending portion 11B.

A treatment tool channel 16 which is a path for feeding a treatment tool such as the medical device 20 is disposed in the insertion portion 11C and the bending portion 11B.

The proximal end portion (at the proximal end side) of the treatment tool channel 16 is connected to a feed port 16a which is open to one side of the insertion portion 11C as shown in FIG. 1.

The treatment tool channel 16 is formed of a flexible tubular member with an inner diameter d1. A distal end portion 16b thereof is connected to the proximal end side of a through-hole portion 12 which axially penetrates the distal end portion 11A and is opened to a distal end surface 11a of the distal end portion 11A as shown in FIG. 3A.

The through-hole portion 12 has a function of an insertion hole through which various treatment tools inserted into the treatment tool channel 16 are inserted. When the medical device 20 is inserted, the through-hole portion has a function of restricting movement of a joint portion of the medical device 20 in calibrating the joint portion of the medical device 20. In this embodiment, the through-hole portion 12 is formed as a cylindrical hole with an inner diameter d0 which is slightly smaller than the inner diameter d1 of the treatment tool channel 16 and a length L. The method of setting the inner diameter d0 and the length L will be described later.

As shown in FIGS. 2 and 3B, the observation unit 15 is a device for observing a treatment target part and includes an imaging mechanism 13 and a lighting mechanism 14 which are known.

The imaging mechanism 13 and the lighting mechanism 14 are disposed in the distal end portion 11A, and an electrical wire or an optical fiber which are not shown are inserted into the bending portion 11B and the insertion portion 11C and is connected to an electrical circuit or a light source in the control unit 5.

The imaging mechanism 13 and the lighting mechanism 14 each have an optical open window on the distal end surface 11a of the distal end portion 11A. Through this open window, external light in front of the distal end portion 11A can be received or illumination light can be emitted forward.

The medical device 20 is an example of a manipulator that moves or drives an end effector at the distal end thereof thanks to a joint portion thereof and is formed in a thin and long shape as a whole.

As shown in FIG. 4, the medical device 20 includes a joint portion 22 that rotates by manipulation of the master arm 3, a shaft-shaped portion 21 that is coupled to the joint portion 22, a grasping portion 26 that grasps a treatment target or the like, a tubular portion 23 that is a flexible tubular portion, and a drive unit 30 that supplies a driving force to the joint portion 22.

The grasping portion 26 is an end effector of the medical device 20 and is attached to the distal end of the shaft-shaped portion 21 at the most distal end side (the distal end side).

The tubular portion 23 is connected to the shaft-shaped portion 21 at the most proximal end side (the proximal end side).

The joint portion 22 is a bending joint and the specific configuration thereof is not particularly limited as long as it is a joint that is bent by transmitting a driving force from the proximal end thereto using a driving force transmission member. The degree of freedom in bending, the bending direction, the degree of bending, and the like of the joint portion 22 are not particularly limited.

Hereinafter, it is assumed that a joint portion 22B that is bent in a direction crossing an extending direction of the medical device 20 and a joint portion 22A that is bent in a direction perpendicular to the bending direction of the joint portion 22B are sequentially arranged from the proximal end side as an example of the joint portion 22.

The joint portions 22B and 22A each have a pulley which is not shown, driving wires 24B and 24A as a driving force transmission member are wound on the pulleys, respectively, and ends thereof are fixed.

In the following description, when the joint portions 22B and 22A or the driving wires 24B and 24A do not have to be distinguished from each other, they may be referred to as the joint portion 22 or the driving wire 24 with subscripts A and B omitted.

The shaft-shaped portion 21 includes shaft-shaped portions 21C and 21B coupled by the joint portion 22B and a shaft-shaped portion 21A coupled to the shaft-shaped portion 21B by the joint portion 22A.

Accordingly, the shaft-shaped portion 21C is a shaft-shaped portion 21 disposed at the most proximal end side of the medical device 20, and an end opposite to the end connected to the joint portion 22B is fixed to the distal end of the tubular portion 23.

The shaft-shaped portion 21A is a shaft-shaped portion 21 disposed at the most distal end side of the medical device 20 and the grasping portion 26 is fixed to the distal end which is an end opposite to the joint portion 22A.

The joint portions 22B and 22A are coupled to both ends of the shaft-shaped portion 21B.

In the following description, a coupled body including the shaft-shaped portion 21C, the joint portion 22B, the shaft-shaped portion 21B, the joint portion 22A, the shaft-shaped portion 21A, and the grasping portion 26 is referred to as a distal-bending portion 25.

Each shaft-shaped portion 21 has an outer diameter D0 which is insertably fitted to an inner diameter d0 of the through-hole portion 12 of the distal end portion 11A.

Each joint portion 22 has a size such that it does not protrude from the outer shape of the coupled shaft-shaped portion 21.

The inner diameter d0 and the length L of the through-hole portion 12 are set to predetermined values with which movement of the joint portion 22 is in a predetermined clearance range when the joint portion 22 and a pair of shaft-shaped portions 21 coupled by the joint portion 22 are inserted into the through-hole portion 12.

For example, in this embodiment, since the through-hole portion 12 has a cylindrical shape, the shaft-shaped portions 21 are arranged coaxially with a straight axis O by setting d0=D0. Accordingly, the joint portion 22 is completely restricted and the bending motion is suppressed.

When the inner diameter d0 is larger than the outer diameter D0, the joint portion 22 moves while the shaft-shaped portion 21 moves in the clearance range. However, when the movement of the shaft-shaped portion 21 in the clearance range ends, the movement of the joint portion 22 is restricted.

In this embodiment, when calibration to be described later is carried out, an operation command for changing a joint angle to cause the joint portion 22 to move in a predetermined bending manner is issued. At this time, when a change $\Delta\theta$ of the joint angle within the clearance range is sufficiently smaller than the change of the joint angle in the operation command, it is possible to cause a calibration error to converge into an allowable range.

The change $\Delta\theta$ is calculated from a relationship of the inner diameter d0 of the through-hole portion 12, the outer diameter D0 of the shaft-shaped portion 21, and the length L of the through-hole portion 12.

For example, when the operation command to change the joint angle in the calibration operation changes the joint angle in a range of $\theta_0$ to $\theta_{max}$, the change $\Delta\theta$ of the joint angle within the clearance range is preferably equal to or less than 30% of a change width ($\theta_{max}-\theta_0$) of the joint angle and more preferably equal to or less than 10% thereof.

The grasping portion 26 includes a pair of grasping members 26a and 26b for holding a treatment tool and a rotating shaft 26c rotatably supporting the grasping members 26a and 26b. The grasping members 26a and 26b rotates about the rotating shaft 26c and moves as indicated by an arrow in FIG. 4 to perform an opening and closing motion by manipulating the gripping manipulation unit, which is not shown, of the master arm 3.

The driving force transmission means of the grasping portion 26 is not particularly limited, but, for example, means of driving a link, which is not shown, coupled to the grasping members 26a and 26b by a manipulation wire which is not shown may be employed.

As shown in FIG. 4, the grasping portion 26 has a size such that it does not protrude from the profile of the shaft-shaped portion 21 coupled thereto when the grasping portion does not grasp an object but is closed.

Accordingly, the distal-bending portion 25 is a shaft-shaped body with a maximum outer diameter D0 and has a shape which can be inserted into the through-hole portion 12 so as to advance and retreat, in a state in which the distal-bending portion is stretched and the grasping portion 26 is closed as described above.

The tubular portion 23 is formed of a soft tubular member such as a resin tube, and an inserted object such as driving wires 24A and 24B for respectively driving the joint portions 22A and 22B is inserted thereinto.

The driving wires 24A and 24B are inserted into sheaths 27 of which both ends are fixed in position between the proximal end portion of the tubular portion 23 and the vicinity of the pulleys at the distal end.

Each sheath 27 is formed of a densely-wound coil or the like having the substantially same diameter as the driving wires 24 and thus the length thereof hardly change even when the sheath is curved with an external force. The inner diameter of the sheath 27 is set to be slightly larger than the outer diameter of the driving wire 24 so as to smoothly pull the driving wire 24.

Examples of the inserted object other than the driving wires 24A and 24B in the tubular portion 23 include manipulation wires for driving the grasping portion 26 and an electrical wire or an optical fiber which is coupled to the observation unit 15, which are not shown.

As shown in FIG. 5, the drive unit 30 includes a body portion 31 that has a driving force transmission mechanism 33 fixed to the proximal end portion of the tubular portion 23 built therein and a detachable portion 32 that is detachably attached to the body portion 31 and has a drive motor 34 (drive unit) built therein.

The attachment and detachment manner of the detachable portion 32 to and from the body portion 31 is not particularly limited as long the driving force of the drive motor 34 can be transmitted to the driving force transmission mechanism 33 at the time of attachment and the detachable portion can be detached for each drive motor 34 at the time of detachment. For example, a method of attaching and detaching housings of the body portion 31 and the detachable portion 32 by concave-convex fitting or screwing or a method of detachably fixing housings of the body portion 31 and the detachable portion 32 via a coupling member such as a screw can be employed.

By detachably attaching the detachable portion 32 in this way, the detachable portion 32 can be detached, for example, when the used distal-bending portion 25 or the tubular portion 23 is disused or sterilized. The detached detachable portion 32 and the detached drive motor 34 can be reused by being attached to a new body portion 31 or a sterilized body portion 31.

The driving force transmission mechanism 33 is a device part that transmits a driving force from the drive motor 34 to the driving wires 24 to pull the driving wire 24, and has the same configuration for the driving wires 24A and 24B. In FIG. 5, only a part pulling the driving wire 24B is shown for the purpose of simplification.

The configurations of the driving force transmission mechanism 33 and the drive motor 34 for driving the driving wire 24B will be described below with reference to FIG. 5, but the same description is applied to the driving force transmission mechanism 33 and the drive motor 34 for driving the driving wire 24A.

The driving force transmission mechanisms 33 (the drive motors 34) may be disposed in separate body portions 31 (detachable portions 32) so as to be individually attached and detached, or all the driving force transmission mechanisms 33 (the drive motors 34) may be fixed to a single body portion 31 (detachable portion 32) so as to be attached and detached as a whole.

In this embodiment, for example, the driving force transmission mechanism 33 employs a rack-and-pinion mechanism including racks 33A and 33B and a pinion 33C.

The racks 33A and 33B are supported to be movable in the pulling direction of the driving wire 24B by a support member, which is not shown, in the body portion 31 and are fixed to the end of the driving wire 24B at ends thereof on the tubular portion 23 side.

The pinion 33C engaging with toothed parts thereof is disposed between the racks 33A and 33B.

The pinion 33C is rotatably supported by a support shaft, which is not shown in the body portion 31. Accordingly, when the rack 33A moves in the direction (see arrow x1 in the drawing) in which the driving wire 24B is pulled to the detachable portion 32, the rack 33B moves in the direction (see an arrow y2 in the drawing) in which it moves away from the detachable portion 32 by the rotation of the pinion 33C. On the contrary, when the rack 33A is pushed in a direction of an arrow x2 in the drawing, the rack 33B moves in a direction of an arrow y1 in the drawing.

The racks 33A and 33B along with the driving wires 24 constitute a driving force transmission member that transmits a driving force generated from the drive motor 34 to the joint portion 22. In this embodiment, the racks 33A and 33B have rigidity higher than that of the driving wire 24 and have elongation in driving smaller than that of the driving wire 24.

The drive motor 34 is a device part that generates a driving force for moving the rack 33A, includes a ball screw 36 that converts a rotational motion into a translational motion, and is detachably coupled to the rack 33A via a tension-measuring unit 35 that measures a tension generated in the driving wire 24B.

The type of the drive motor 34 is not particularly limited as long as it can move the ball screw 36 by only a predetermined distance by rotating by only a predetermined degree of rotation based on an operation command value. For example, a servo motor, a stepping motor, or a DC motor can be employed.

In this embodiment, a DC servo motor including an encoder 34a that detects a degree of rotation is employed as the drive motor 34.

The drive motor 34 is coupled to the control unit 5 in a communicable manner as shown in FIG. 6.

The tension-measuring unit 35 is not particularly limited as long as it can measure a tension generated in the driving wire 24B. In this embodiment, for example, a load cell that is fixed to an end of the ball screw 36 and is detachably coupled to the rack 33A is employed.

The tension-measuring unit 35 is connected to the control unit 5 in a communicable manner.

The functional configuration of the control unit 5 will be described below with a focus on the functional configuration of a part that performs operation control and calibration control of the joint portions 22.

As shown in FIG. 6, the control unit 5 includes a motor control unit 100 (control unit), a calibration control unit 101 (control unit), and a storage unit 102.

The motor control unit 100 serves to analyze a motion of the joint portion of the master arm 3 which is output from the master arm 3, to calculate a rotation angle of the joint portion 22 for making the same motion, and controls a degree of rotation of the drive motor 34 corresponding thereto. Details of the control which is performed by the motor control unit 100 will be described later along with description of the operation thereof.

The calibration control unit 101 serves to perform a calibration operation of the joint portion 22 of the medical device 20 and to causes the motor control unit 100 to set a control parameter of the drive motor 34 which is acquired by the calibration operation as a main-driving control parameter.

In the calibration operation, first, the drive motor 34 is actuated based on a calibration drive pattern stored in the storage unit 102. At this time, a load generated in the medical device 20 is measured and the main-driving control parameter is determined based on the load.

In this embodiment, tension information of the driving wire 24 which is measured by the tension-measuring unit 35 is employed as the load and the tension-measuring unit 35 configurations a load-measuring unit.

Accordingly, the calibration control unit 101 is connected to the motor control unit 100, the storage unit 102, and the tension-measuring unit 35 in a communicable manner.

Details of the control which is performed by the calibration control unit 101 will be described later along with description of the operation thereof.

In this embodiment, the motor control unit 100X) and the calibration control unit 101 constitute a control unit that performs operation control of the drive motor 34 and setting of a control parameter.

The storage unit 102 is a device part that stores a predetermined calibrating drive pattern and control parameter determination information for determining the main-driving control parameter based on a load and is connected to the calibration control unit 101 in a communicable manner.

Examples of the information stored in the storage unit 102 will be described later along with description of the operation thereof.

The configuration of the control unit 5 is constituted by a computer including a CPU, a memory, an input/output interface, and an external memory device, and an appropriate control program for realizing the above-mentioned control functions is executed by the computer.

With this configuration, the medical device 20, the motor control unit 100, the calibration control unit 101, the tension-measuring unit 35, and the storage unit 102 constitute the manipulator according to this embodiment.

The operation of the medical device 20 of the manipulator system 1 will be described below.

Figure 7:
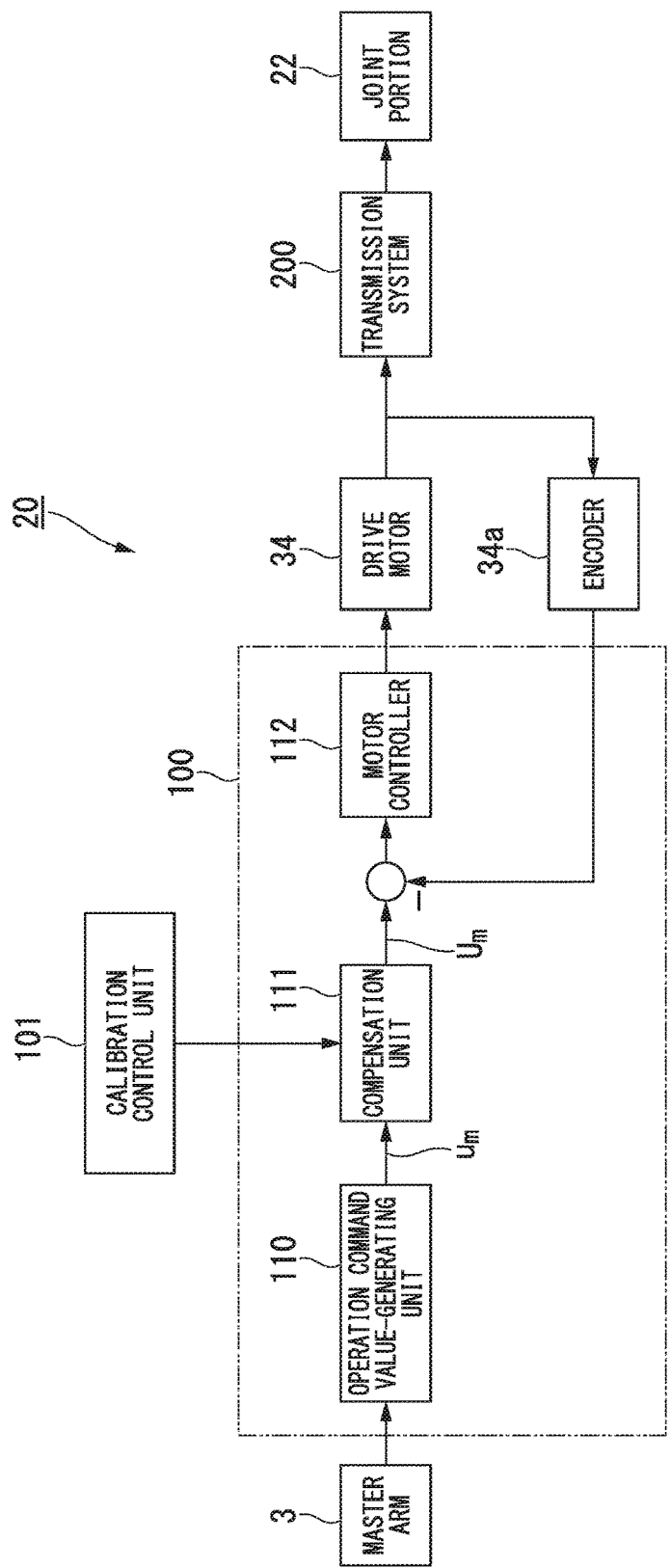
FIG. 7 is a control block diagram of the manipulator according to the first embodiment of the present invention.
Figure 8:
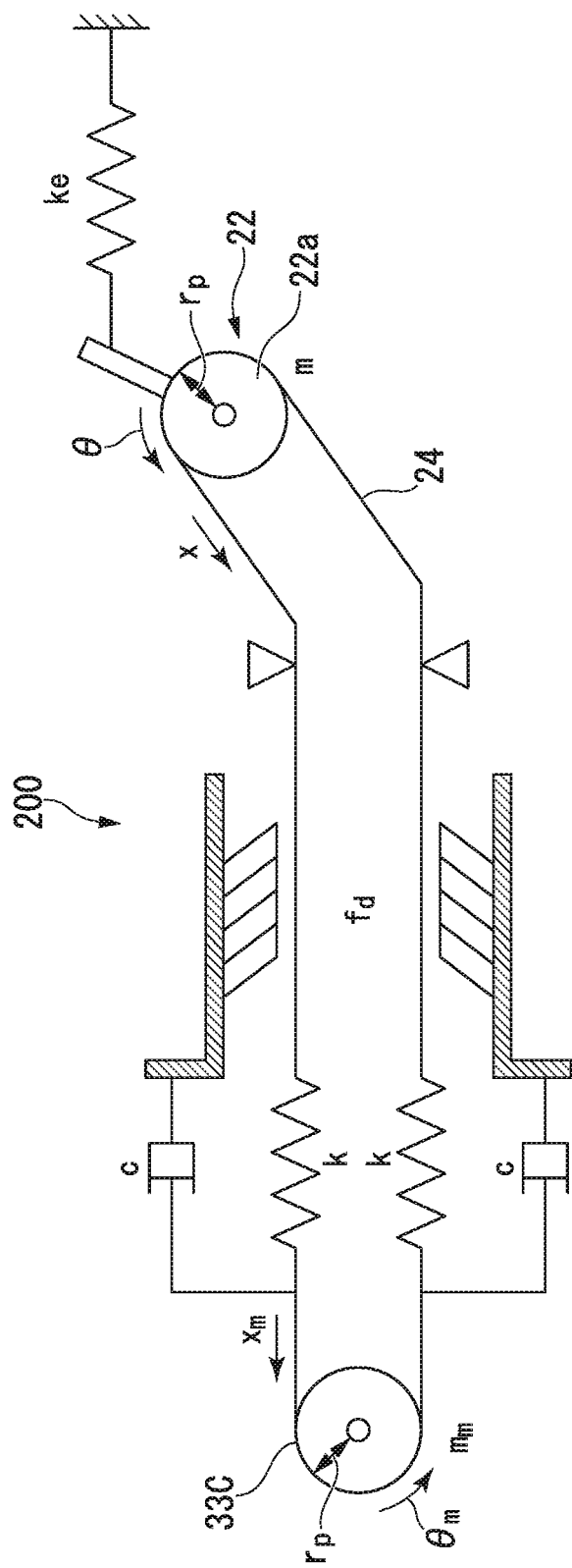
FIG. 8 is a schematic diagram showing a model of a transmission system in the manipulator according to the first embodiment of the present invention.

FIG. 7 is a control block diagram of the manipulator according to the first embodiment of the present invention. FIG. 8 is a schematic diagram showing a model of a transmission system of the manipulator according to the first embodiment of the present invention.

When treatment is performed using the medical device 20 of the manipulator system 1, the distal end portion of the medical device 20 is first inserted into the body of a patient Pa and is sent to the vicinity of a treatment target part using the outer sheath 11 of the treatment endoscope device 10.

At this time, since the outer sheath 11 is curved along an insertion path in the body, the treatment tool channel 16 in the outer sheath 11 and the tubular portion 23 of the medical device 20 which is inserted thereinto are also curved.

Accordingly, the sheaths 27 and the driving wires 24 which are inserted into the tubular portion 23 are also curved. In general, the curving method varies between the driving wires 24 which move in parallel.

When the driving wires 24 are pulled in the curved sheaths 27, a sliding load varies due to a difference in a degree of curving between the sheaths 27 and the driving wires 24 are elongated or loosened depending on the insertion parts. Accordingly, transmission of a driving force is delayed, an amount of force acting on the joint portion 22 decreases, or backlash occurs when the driving direction of the joint portion 22 is changed.

Particularly, one of the driving wires 24 which are disposed in parallel is located inside the curve and the other thereof is located outside the curve to pull the pulleys of the joint portion 22, a difference in sliding load depending on the pulling direction (the rotating direction of the joint portion 22) becomes marked and thus such a problem is likely to occur.

When this problem occurs, the degree of rotation of the pinion 33C pulling the driving wire 24 does not accurately correspond to the degree of rotation of the pulley of the joint portion 22 and thus it is not possible to perform driving accurately corresponding to the manipulation input of the master arm 3.

Therefore, in the medical device 20 according to this embodiment, the degree of rotation of the pinion 33C and the degree of rotation of the pulley of the joint portion 22 are matched by performing a calibration method according to this embodiment to change the control parameter of the drive motor 34 based on the load generated in the medical device 20 before mainly driving the medical device 20.

The control of the main driving of the medical device 20 will be described below with reference to FIG. 7.

When a manipulation input from the master arm 3 is sent out to the motor control unit 100, an operation command value $u_m$ of the drive motor 34 based on the joint structure of the medical device 20 is generated by an operation command value-generating unit 110 of the motor control unit 100.

The operation command value $u_m$ is an operation command value which can accurately drive the joint portion 22 when a transmission system 200 between the pinion 33C and the joint portion pulley 22a disposed in the joint portion 22 based on the drive motor 34 has transmission characteristics that an external load due to curving of the driving wire 24 is not generated.

However, in the transmission system 200, an external load is generated depending on the curved state of the sheath 27 in use.

For example, as shown in FIG. 8, when the driving wire 24 with a spring stiffness (spring constant) k and a viscous damping constant c is pulled by the pinion 33C and the racks 33A and 33B which are not shown, the transmission system 200 can be modeled as a dynamic system in which coulomb friction acts on the driving wire 24 depending on a curved state from the curved sheath 27 or the like. In FIG. 8, a pitch radius of the pinion 33C and a pitch radius of the joint portion pulley 22a are set to the same as $r_p$ for the purpose of simplification. In this embodiment, the spring stiffness of the racks 33A and 33B is sufficiently larger than that of the driving wire 24 and thus is ignored.

The equations of motion of the model can be expressed by Equations (1) to (4).

$$I_m \cdot \left(\frac{\ddot{x}_m}{r_p}\right) = -k(x_m - x) \cdot r_p + N_m \quad (1)$$

$$I \cdot \left(\frac{\ddot{x}}{r_p}\right) = \{-k(x - x_m) - k_e x - c\dot{x} - \text{sgn}(f_d)\} \cdot r_p \quad (2)$$

$$x_m = r_p \theta_m \quad (3)$$

$$x = r_p \theta \quad (4)$$

Here, the symbol $\theta_m$ denotes a degree of rotation of the pinion 33C, the symbol $\theta$ denotes a degree of rotation of the joint portion pulley 22a, the symbol $N_m$ denotes a driving torque of the drive motor 34, the symbol $I_m$ denotes a moment of inertia of the drive motor 34 and the driving force transmission mechanism 33, the symbol I denotes a moment of inertia of a driven part of the joint portion 22, the symbol $f_d$ denotes a coulomb frictional force applied to the driving wire 24, and the symbol $k_e$ denotes an environmental stiffness which is obtained by modeling an external force acting on the joint portion 22.

Here, the symbol sgn denotes a sign function that is designed to +1, 0, or −1 depending on the plus, 0, or minus of a function.

When coulomb friction acts on the driving wire 24 depending on the curved state, the degree of rotation $\theta_m$ of the pinion 33C and the degree of rotation $\theta$ of the joint portion pulley 22a are not equal to each other. Since it is difficult to predict the curved state in advance, an actual load in the transmission system 200 is measured and a calibration operation of compensating for the load is performed in a curved state in a usable state in this embodiment.

Accordingly, the motor control unit 100 includes a compensation unit 111 that converts the operation command value $u_m$ determined by the operation command value-generating unit 110 into a value for compensating for the load applied to the driving wire 24.

In this embodiment, the operation command value $u_m$ is generated by adding a compensation value up to the operation command value $u_m$ of the degree of rotation of the drive motor 34 output from the operation command value-generating unit 110.

The compensation value $u_F$ is set in the motor control unit 100 in advance by the calibration control unit 101 until the main driving is started.

The operation command value $u_m$ and the compensation value up are expressed by Equations (5) and (6).

$$U_m = u_m + u_F \quad (5)$$

$$u_F = \frac{1}{r_p} \cdot \frac{f_d}{k} \cdot \text{sgn}(\dot{\theta}_{ref}) \quad (6)$$

Here, the symbol $\theta_{ref}$ denotes the operation command value $u_m$.

In this way, in this embodiment, the sign of the compensation value $u_F$ is determined depending on the sign of the time integration of $\theta_{ref}$. Accordingly, the operation command value $u_m$ is generated such that the driving wire 24 is always more actuated in the opposite direction of the direction in which the coulomb friction acts.

When the operation command value $u_m$ is output to a motor controller 112, the drive motor 34 is driven based on the operation command value $u_m$. The degree of rotation of the drive motor 34 is detected by the encoder 34a and is controlled in a feedback manner.

In this way, the driving wire 24 is pulled based on the operation command value $u_m$ which is obtained by expecting the load of the transmission system 200 and thus the joint portion 22 is driven.

Accordingly, an operator Op can perform necessary treatment using the medical device 20.

The calibration method of setting the compensation value $u_F$ according to this embodiment will be described below.

Figure 9:
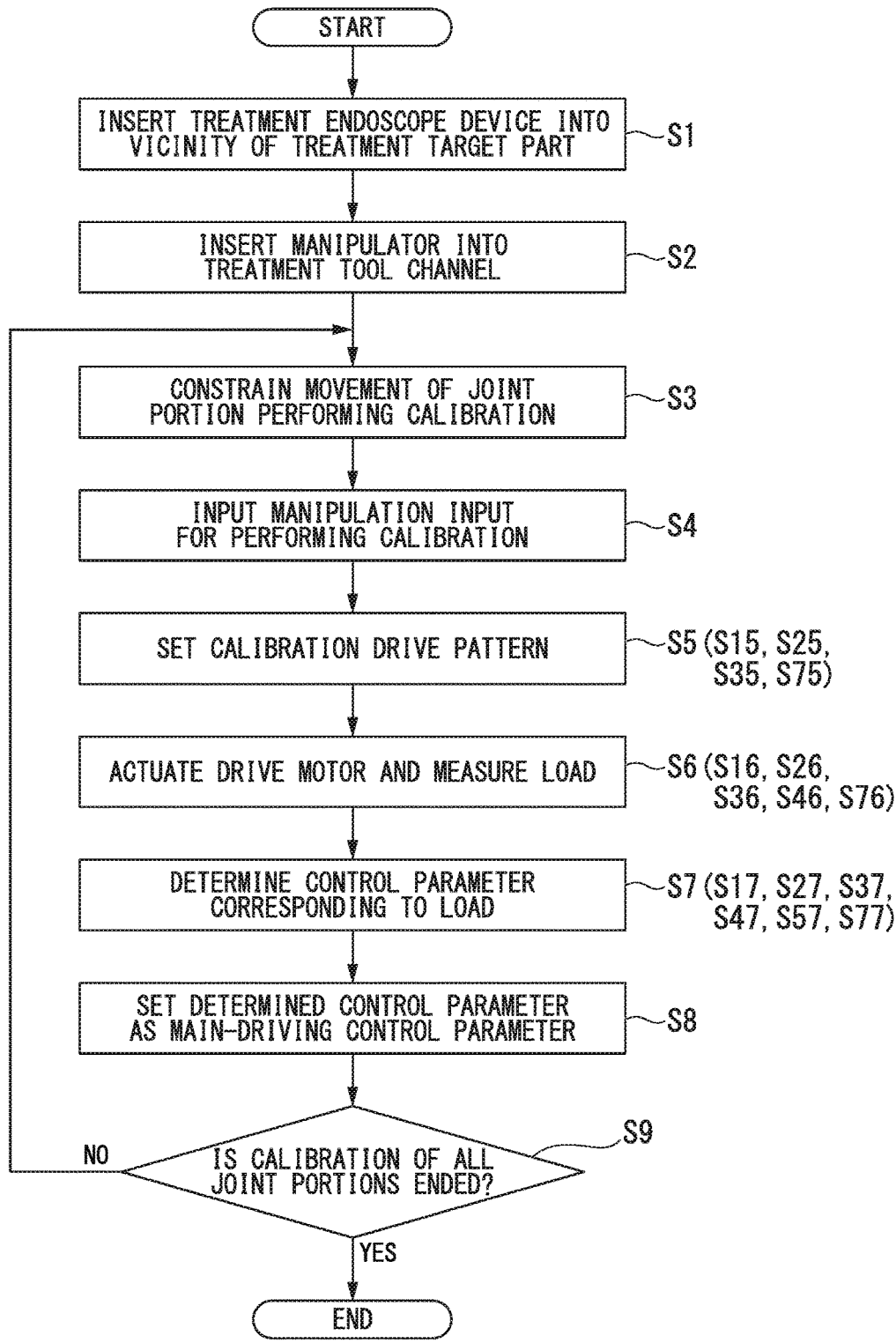
FIG. 9 is a flowchart showing a flow of a method of calibrating the manipulator according to the first embodiment of the present invention.
Figure 10A:
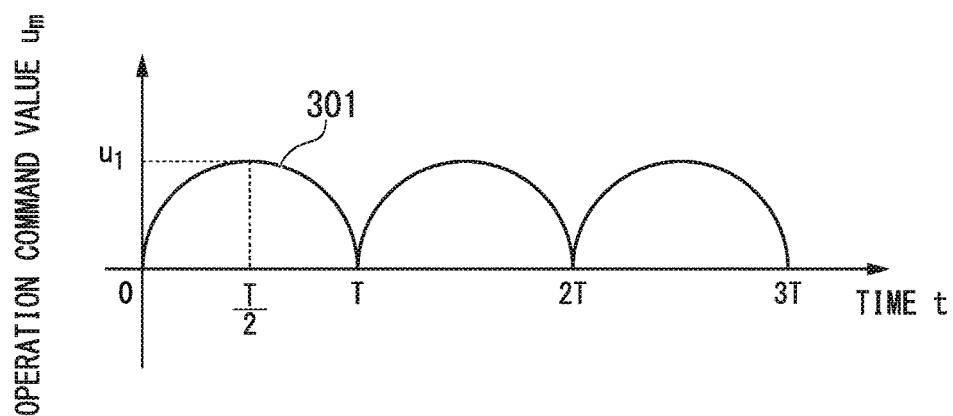
FIG. 10A is a schematic graph showing an example of a drive pattern which is used in the method of calibrating the manipulator according to the first embodiment of the present invention.
Figure 10B:
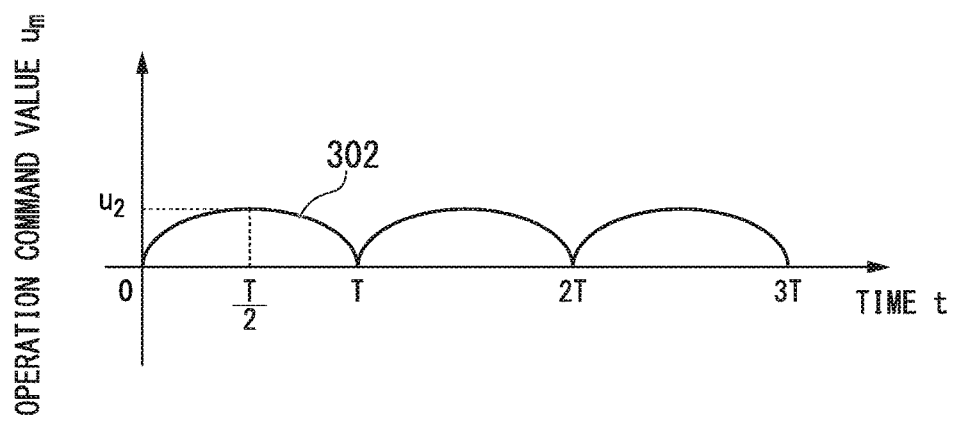
FIG. 10B is a schematic graph showing an example of a drive pattern which is used in the method of calibrating the manipulator according to the first embodiment of the present invention.
Figure 11:
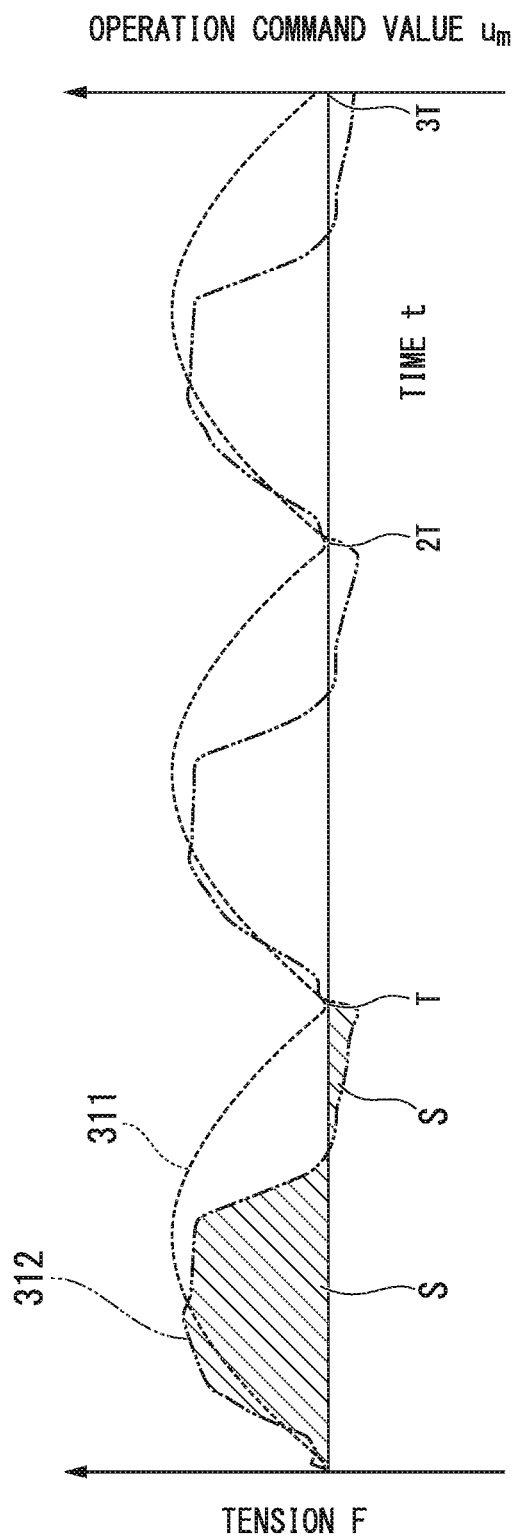
FIG. 11 is a graph showing an example of a load measurement result of the manipulator according to the first embodiment of the present invention.

FIG. 9 is a flowchart showing a flow of the method of calibrating the manipulator according to the first embodiment of the present invention. FIGS. 10A and 10B are schematic graphs showing examples of the drive pattern which is used in the method of calibrating the manipulator according to the first embodiment of the present invention. FIG. 11 is a graph showing an example of the operation command value and the tension measurement result in the manipulator according to the first embodiment of the present invention. The horizontal axis represents time t, the left side of the vertical axis represents a tension F, and the right side thereof represents an operation command value $u_m$.

The calibration method according to this embodiment is performed by performing steps S1 to S9 shown in FIG. 9 along the flow of FIG. 9.

Step S1 is a step of inserting the treatment endoscope device 10 to the vicinity of a treatment target part.

The outer sheath 11 of the treatment endoscope device 10 is inserted into the body of a patient Pa and the treatment endoscope device 10 is located in the vicinity of the treatment target part.

This is the end of step S1.

Then, step S2 is performed. This step is a step of inserting the medical device 20 as a manipulator into the treatment tool channel 16 of the treatment endoscope device 10.

The distal-bending portion 25 of the medical device 20 is inserted into the feed port 16a by an operator Op, an insertion robot which is not shown, or the like, and the medical device 20 is fed through the treatment tool channel 16 until the distal-bending portion 25 is inserted into the through-hole portion 12.

Accordingly, the tubular portion 23 of the medical device 20 is curved depending on the curved state of the treatment tool channel 16.

This is the end of step S2.

Steps S1 and S2 constitute an arrangement step of arranging the medical device 20 in a usable state. When it is actually intended to perform treatment using the medical device 20, the distal-bending portion 25 needs to protrude to the front side of the distal end surface 11a of the treatment endoscope device 10 as shown in FIG. 2, but the tubular portion 23 is longer than the distal-bending portion 25. Accordingly, in the state in which the distal end of the distal-bending portion 25 stays in the through-hole portion 12 and the state in which the distal-bending portion 25 protrudes from the through-hole portion 12 as shown in FIG. 2, the curved states thereof are substantially equal to each other and the loads generated in the driving wire 24 are substantially equal to each other.

As described above, in the arrangement step of this embodiment, the medical device 20 is arranged after the treatment endoscope device 10 is inserted into the body. However, by inserting the medical device 20 into the treatment tool channel 16 of the treatment endoscope device 10 in advance, the medical device 20 may be arranged in the usable state by inserting the medical device 20 into the body of the patient Pa along with the treatment endoscope device 10.

Then, step S3 is performed. This step is a step of restricting movement of the joint portion 22 to be calibrated.

In this embodiment, since the joint portion 22 includes two joint portions 22A and 22B, the joint portions are individually calibrated. The calibration order is not particularly limited.

Means for restricting the joint portion 22 is not particularly limited, but the restriction is performed by inserting the joint portion 22 and the shaft-shaped portion 21 adjacent thereto into the through-hole portion 12 in this embodiment.

For example, first, a degree of insertion of the medical device 20 is adjusted such that the joint portion 22A and at least a part of the shaft-shaped portion 21A and 21B are located inside the through-hole portion 12.

Accordingly, even when the joint portion 22A is driven, the shaft-shaped portions 21A and 21B can move within only the clearance range from the through-hole portion 12 and thus the movement of the joint portion 22A is restricted.

Accordingly, since the environmental stiffness $k_e$ in Equation (2) is fixed, it is possible to more accurately measure the load corresponding to the curved state.

This is the end of step S3.

Then, step S4 is performed. This step is a step of performing a manipulation input for calibration.

In this embodiment, an operator Op manipulates the push button manipulation unit of the master arm 3.

This manipulation input is output to the calibration control unit 101 of the control unit 5.

This is the end of step S4.

When step S4 ends, the calibration control unit 101 performs step S5.

This step is a step of setting a calibrating drive pattern.

The calibration control unit 101 reads a calibrating drive pattern stored in advance in the storage unit 102.

Then, the calibration control unit 101 sets $u_F=0$ for the compensation unit 111 of the motor control unit 100.

This is the end of step S5.

The calibrating drive pattern will be described below.

The calibrating drive pattern is a preset drive pattern for measuring a load in the curved state of the medical device 20.

This drive pattern may be a drive pattern common to the joint portions 22, but may be set as different drive patterns to accurately detect a load when the joint portions 22 have a difference in a degree of operation or a structure.

In order to improve measurement accuracy of a load, it is preferable that the drive pattern be a drive pattern in which a predetermined pattern is periodically repeated.

In this embodiment, two types of drive patterns 301 and 302 as shown in FIGS. 10A and 10B are prepared.

The drive pattern 301 shown in FIG. 10A is used, for example, to calibrate the joint portion 22A and is a pattern in which a mountain-shaped pattern in which the operation command value $u_m$ increases from 0 to a maximum value $u_1$ and is then returned to 0 with the lapse of time is repeated with a cycle T. The number of cycles is not particularly limited and is set to, for example, three in FIG. 10A.

Here, a changing rate $u_m'$ of the operation command value $u_m$ is not particularly shown, but the operation command value changes to have the maximum value at time t=0 and 0 at time t=T/2 and to change from the minimum value to the maximum value at time t=T.

The drive pattern 302 shown in FIG. 10B is used, for example, to calibrate the joint portion 22B and is a pattern in which the maximum value $u_1$ of the operation command value $u_m$ of the drive pattern 301 is replaced with $u_2$ (where $u_2<u_1$).

Then, step S6 is performed. This step is a step of driving the drive motor 34 based on the calibrating drive pattern and measuring a load.

The calibration control unit 101 outputs the operation command value $u_m$ based on the drive pattern read from the storage unit 102 in step S5 to the motor control unit 100.

Accordingly, $U_m=u_m$ is output to the motor controller 112 and the drive motor 34 is driven.

For example, when the joint portion 22A is first calibrated, the drive motor 34 for driving the joint portion 22A is driven based on the operation command value $u_m$ based on the drive pattern 301 shown in FIG. 10A.

When this driving is started, a driving load is measured by the load-measuring unit.

In this embodiment, as shown in FIG. 6, the tension-measuring unit 35 is employed as the load-measuring unit and the tension generated in the driving wire 24 at the time of driving is measured by the tension-measuring unit 35. The measured tension is sequentially output to the calibration control unit 101.

The calibration control unit 101 calculates the load from the output tension information.

The larger the tension becomes, the larger the load corresponding to the curved state becomes. Accordingly, in this embodiment, an integrated value of the tension is calculated and used as the load.

For example, when the operation command value $u_m$ is a curve 311 as shown in FIG. 11 and the tension F(t) is measured as a curve 312 shown in FIG. 11, an integrated area per unit cycle as indicated by the hatched part is calculated and is set as the load S. That is, when the number of cycles is set to n (n=3 in this embodiment), the load S is calculated by performing an integrating operation of Equation (7).

This is the end of step S6.

$$S = \frac{1}{n}\sum_{i=1}^{n} \int_{(i-1)T}^{iT} |F(t)| dt \qquad (7)$$

In this way, by calculating the load S as the tension integrated value, a measurement error of the tension is averaged. Accordingly, it is possible to accurately calculate the load S.

Steps S5 and S6 constitute a load-measuring step of issuing an operation command based on a predetermined calibrating drive pattern to the drive motor 34 and measuring a load generated in the medical device 20 at that time.

Step S3 constitutes a joint portion-restricting step of restricting movement of the joint portion 22 before performing the load-measuring step.

Then, step S7 is performed. This step is a step of determining a control parameter corresponding to the load. Particularly, in this embodiment, the control parameter is determined with reference to control parameter determination information. The control parameter determination information is information for determining the compensation value $u_F$ based on the load S measured in step S6, is acquired before the calibrating operation, and is stored in the storage unit 102.

A method of calculating the control parameter determination information in this embodiment will be described below.

Figure 12A:
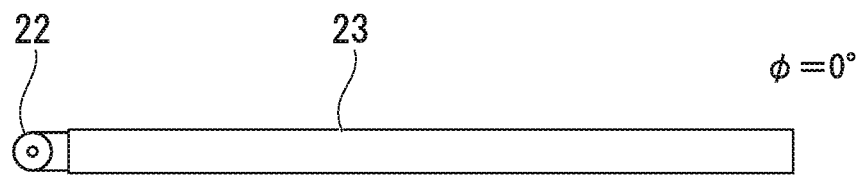
FIG. 12A is a schematic diagram showing a load-applying method for acquiring control parameter determination information in the method of calibrating the manipulator according to the first embodiment of the present invention.
Figure 12B:
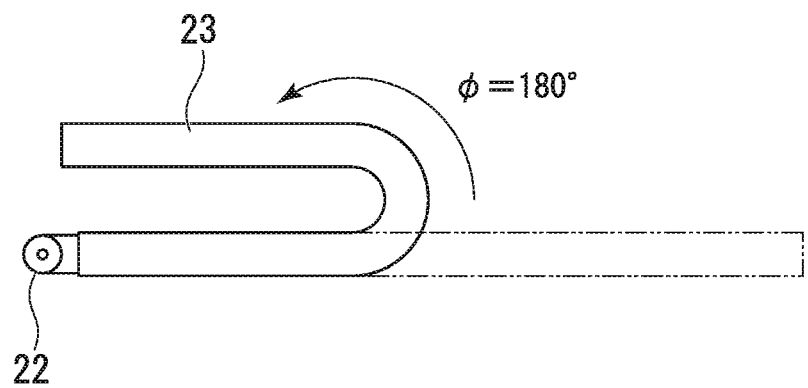
FIG. 12B is a schematic diagram showing a load-applying method for acquiring control parameter determination information in the method of calibrating the manipulator according to the first embodiment of the present invention.
Figure 12C:
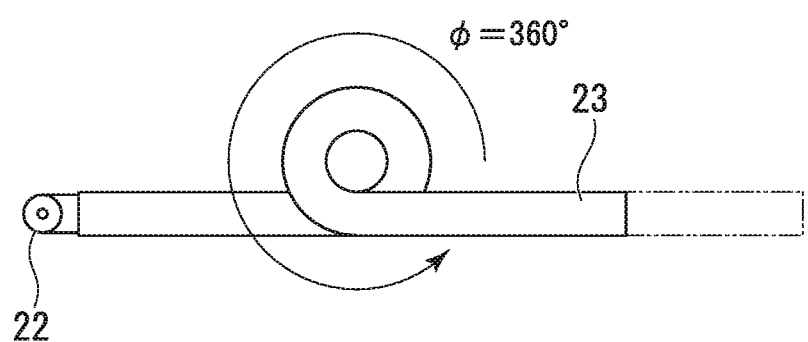
FIG. 12C is a schematic diagram showing a load-applying method for acquiring control parameter determination information in the method of calibrating the manipulator according to the first embodiment of the present invention.
Figure 14A:
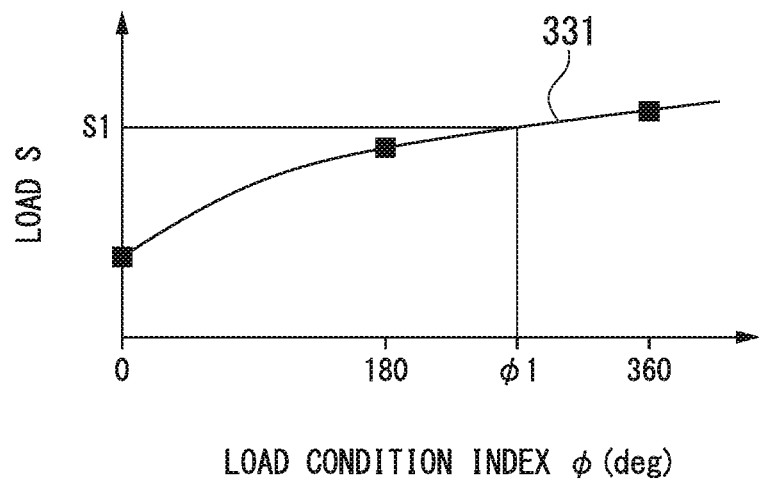
FIG. 14A is a schematic graph showing an example of the control parameter determination information in the method of calibrating the manipulator according to the first embodiment of the present invention.
Figure 14B:
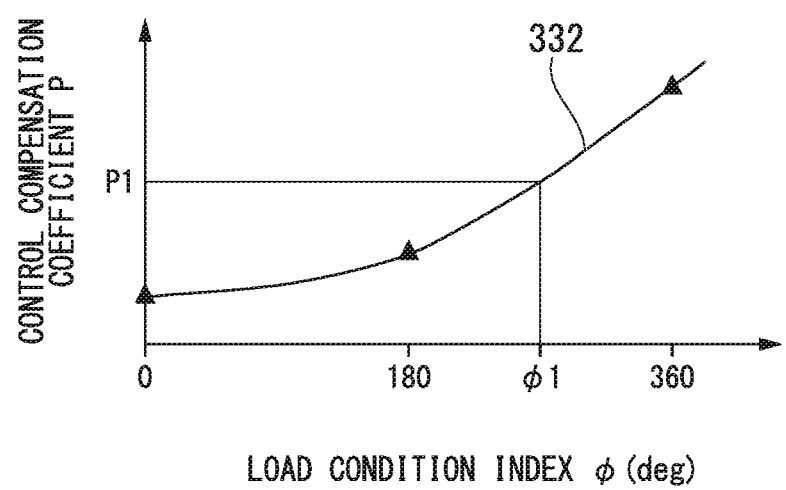
FIG. 14B is a schematic graph showing an example of the control parameter determination information in the method of calibrating the manipulator according to the first embodiment of the present invention.

FIGS. 12A to 12C are schematic diagrams showing a load-applying method for acquiring the control parameter determination information in the method of calibrating the manipulator according to the first embodiment of the present invention. FIG. 13 is a graph showing an example of a change of a tension due to a difference in load condition of the manipulator according to the first embodiment of the present invention. The horizontal axis represents time t, the left side of the vertical axis represents the tension F, and the right side thereof represents the operation command value $u_m$. FIGS. 14A and 14B are schematic graphs showing an example of the control parameter determination information in the method of calibrating the manipulator according to the first embodiment of the present invention. The horizontal axes in both diagrams represent a load state index (deg), the vertical axis in FIG. 14A represents the load S, and the vertical axis in FIG. 14B represents a control compensation coefficient P.

As the control parameter, the spring stiffness k and the coulomb frictional force $f_d$ which are unknown parameters in Equation (6) may be determined, but these are consolidated into the control compensation coefficient P in this embodiment.

Accordingly, in this embodiment, first, driving is performed based on the calibrating drive pattern and the load S is measured in the same way as in steps S3 to S6 in a state in which the curved state of the medical device 20 is changed and the load is changed.

At this time, the curved state to be set may be determined based on curved states which are possible in a usable state, but it is important to widely change the magnitude of the load in order to cope with various curved states in at usable state. Accordingly, it is not necessary to match the curved states in a usable state.

For example, as shown in FIGS. 12A, 12B, and 12C, the load can be changed by forming a bending portion in the middle of the length direction of the tubular portion 23. In this case, the degree of load in each curved state corresponds to an angle φ formed by the tubular portion 23 with the bending portion interposed therebetween.

In the following description, the angle φ is referred to as a load condition index. The load condition index φ can be a quantity corresponding to the load one to one.

The load condition shown in FIG. 12A is a state in which the tubular portion 23 is straightened and φ=0 (the unit of which is ° which is true of the following description) is set.

The load condition shown in FIG. 12B is a curved state in which the tubular portion 23 is bent at 180° in the middle thereof φ=180(°) is set.

The load condition shown in FIG. 12C is a curved state in which the tubular portion 23 is wound by one turn in the middle thereof and φ=360(°) is set.

Similarly, a proper load condition index φ can be set as necessary.

FIG. 13 shows an example in which a change in tension is measured in such load conditions. In FIG. 13, a curve 321 indicates the same operation command value $u_m$ as in the curves 301 and 311 in FIGS. 10A and 11.

A curve 322 indicates a change in tension F at φ=0(°), a curve 323 indicates a change in tension F at φ=180 (°), and a curve 324 indicates a change in tension F at φ=360 (°). It can be seen that the tension F increases with an increase of the load condition index φ.

In this way, the load S is calculated as S=300 (N·s) at φ=0 (°), as S=900 (N·s) at φ=180 (°), and as S=1200 (N·s) at φ=360 (°).

By collecting these data, the graph shown in FIG. 14A is obtained. By calculating an approximate curve 331 from the data, the load S(φ) corresponding to the proper load condition index φ which is not actually measured can be estimated.

Then, the condition of the control compensation coefficient P in which the same operation as the curve 321 in FIG. 13 is realized is calculated in each load condition.

In this embodiment, driving is performed while changing the control compensation coefficient P in the load conditions and the proper control compensation coefficient P(φ) is calculated.

In the above-mentioned specific example, P(0)=1.5 (rad), P(180)=4.0 (rad). P(360)=10.5 (rad) are calculated.

By collecting these data, the graph shown in FIG. 14B is obtained. By calculating an approximate curve 332 from the data, the control compensation coefficient P(φ) corresponding to the proper load condition index φ which is not actually measured can be estimated.

Equations of the approximate curves 331 and 332 which are obtained in this way or a data table corresponding to the equations are stored as the control parameter determination information in the storage unit 102. Accordingly, the calibration control unit 101 can determine a proper control compensation coefficient P based on the load S measured in step S6.

For example, when the load S in step S6 is S1 as shown in FIGS. 14A and 14B, the load condition index φ becomes φ1 from the approximate curve 331 and the control compensation coefficient P is calculated as P=P1 by substituting φ1 for the approximate curve 332. In the above-mentioned specific example, φ1=234 (deg) and P1=5.44 (rad) are calculated at S1=1022 (N·s).

When the control parameter determination information is given as the data table, the control compensation coefficient P1 is calculated from the load S1 in the same way by appropriately interpolating the data values.

In this way, when the control parameter corresponding to the load S calculated in step S6 is determined as the control compensation coefficient P, step S7 ends.

Then, step S8 is performed. This step is a step of setting the determined control parameter as the main-driving control parameter.

The calibration control unit 101 outputs the determined control compensation coefficient P to the compensation unit 111 of the motor control unit 100.

This is the end of step S8.

Accordingly, when a manipulation input is performed by the master arm 3, the compensation value $u_F$ based on Equation (8) is added to the operation command value $u_m$ corresponding to the manipulation input and the drive motor 34 is driven using the operation command value $u_m$ based on Equation (5).

$$u_F = P \cdot \mathrm{sgn}(\dot{\theta}_{ref}) \qquad (8)$$

Steps S7 and S8 constitute a control parameter-setting step of setting the main-driving control parameter based on the load measured in the load-measuring step.

Then, step S9 is performed. This step is a step of determining whether the calibration of all the joint portions 22 is completed.

When a joint portion 22 of which the calibration is not completed yet is present, the flow moves to step S3 and steps S3 to S9 are repeatedly performed on the joint portion 22 of which the calibration is not completed.

When the calibration of all the joint portions 22 is completed, the calibration of this embodiment ends.

The operation of this calibration will be described below.

Figure 15:
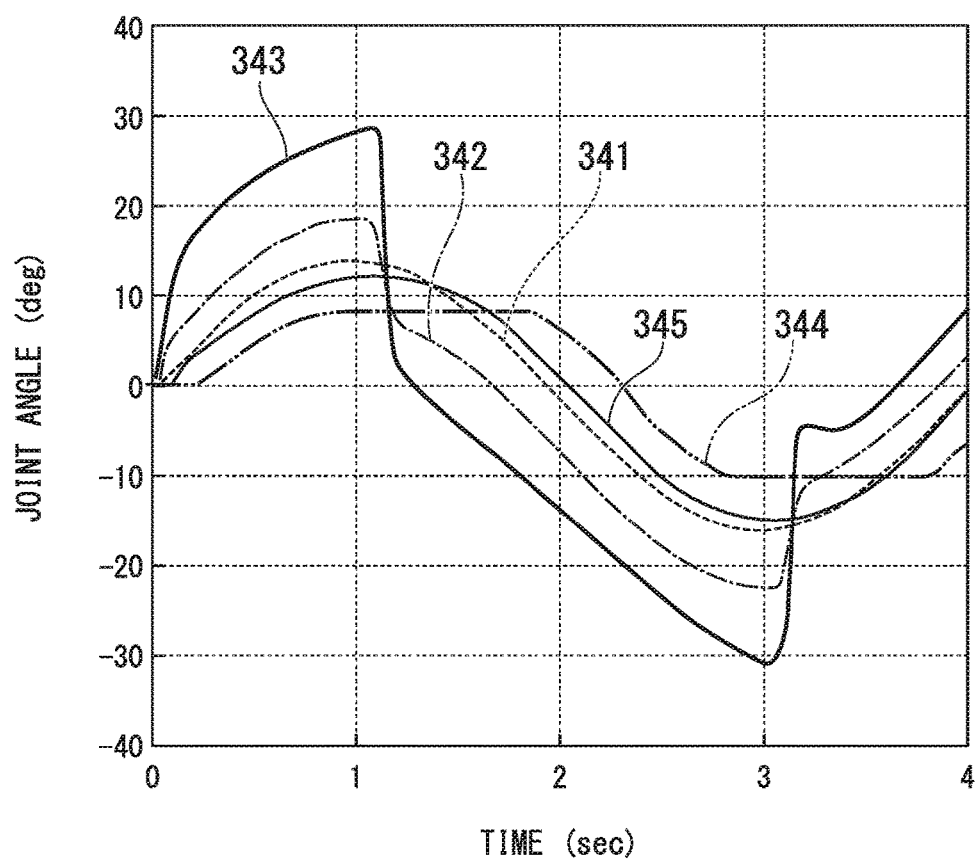
FIG. 15 is a graph showing an example of an operation command value of a drive motor and a response of a joint portion in the method of calibrating the manipulator according to the first embodiment of the present invention.

FIG. 15 is a graph showing an example of the operation command value of the drive motor and a response of a joint portion in the method of calibrating the manipulator according to the first embodiment of the present invention. The horizontal axis represents the time (sec) and the vertical axis represents the joint angle (deg).

In FIG. 15, the operation command value of the drive motor 34 and the joint angle of the joint portion 22 are shown, but the operation command value is converted to correspond to the joint angle for the purpose of easy comparison.

For example, when the joint portion 22 is driven to reciprocate within a joint angel range of ±15 as indicated by a curve 341 in FIG. 15, the operation command value $u_m$ of the drive motor 34 is set to a curve 342 in consideration of non-load transmission characteristics of the transmission system 200.

However, when the load condition of the transmission system 200 is changed by curving the tubular portion 23, an operation of following the curve 341 cannot be realized with the operation command value $u_m$ as indicated by a curve 344.

In this embodiment, the above-mentioned calibration is performed to add the compensation value $u_F$ and thus the operation command value $u_m$ is set as indicated by a curve 343.

At this time, the response of the joint portion 22 is substantially matched with the curve 341 as indicated by a curve 345.

In the calibration method according to this embodiment, the medical device 20 is driven using the calibrating drive pattern in an arrangement in a usable state, the load generated in the manipulator is measured, and the main-driving control parameter is set based on the load. Accordingly, even when a load is applied to the driving force transmission member depending on the arrangement in a usable state, it is possible to easily perform calibration for accurately driving the joint portion.

This calibration can be performed as necessary in a state in which the medical device 20 is disposed in the body of a patient Pa. Accordingly, even when the load condition is changed in use, it is possible to perform calibration corresponding to the load condition. As a result, for example, even when the load condition is changed due to repeated manipulation or the like, it is possible to cause the joint portion to accurately operate.

Regarding the control parameter determination information which is used for the calibration method according to this embodiment, proper control parameters in a plurality of load conditions are acquired in advance and proper values of the control parameters corresponding to the other loads can be rapidly determined from the control parameters.

In the medical device 20 according to this embodiment, the tension-measuring unit 35 as the load-measuring unit is disposed in the detachable portion 32 of the drive unit 30 which is located outside a patient Pa at the proximal end side of the medical device 20. Accordingly, it is possible to accurately measure the load without an increase in size of the joint portion 22. Even when a part of the medical device 20 which is located at the distal end side of the body portion 31 is not reused but is disused, the tension-measuring unit 35 can be reused along with the drive motor 34 and it is thus possible to use the medical device with a low cost.

In the medical device 20 according to this embodiment, the operation of the joint portion 22 of the medical device 20 can be controlled by only controlling the drive motor 34. Accordingly, a joint angle sensor does not have to be disposed in the joint portion 22 and thus the joint portion 22 can be constructed with a low cost.

First Modified Example

A method of calibrating a manipulator according to a first modified example of the first embodiment will be described below.

Figure 16:
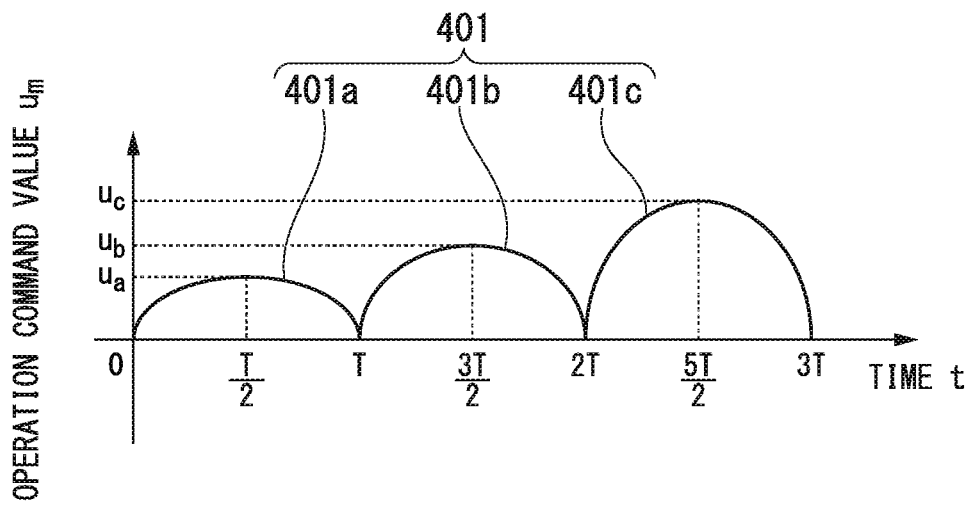
FIG. 16 is a schematic graph showing an example of a drive pattern which is used in a method of calibrating a manipulator according to a first modified example of the first embodiment of the present invention.

FIG. 16 is a schematic graph showing an example of a drive pattern which is used in the method of calibrating a manipulator according to the first modified example of the first embodiment of the present invention. The horizontal axis represents the time t and the vertical axis represents the operation command value $u_m$.

The method of calibrating a manipulator according to this modified example is a modified example in which the drive pattern in the first embodiment is changed and is a method which can be applied to calibration of the medical device 20 in the manipulator system 1 according to the first embodiment.

In this modified example, the control unit 5 includes a calibration control unit 101A (control unit) instead of the calibration control unit 101 in the first embodiment as shown in FIG. 6.

As shown in FIG. 16, the storage unit 102 stores a plurality of patterns in which the maximum value of the mountain-shaped pattern in the drive pattern 301 in the first embodiment is changed.

For example, a drive pattern 401 shown in FIG. 16 includes patterns 401a, 401b, and 401c in which the maximum value of the operation command value $u_m$ in the cycles is changed in an ascending order such as $u_a$, $u_b$, and $u_c$ in the same mountain-shaped pattern as the drive pattern 301.

The calibration method according to this modified example using the drive pattern 401 will be described below with a focus on a difference from the first embodiment.

The calibration method according to this modified example is different from the calibration method according to the first embodiment in that the operation of the calibration control unit 101 is performed by the calibration control unit 101A in the flow of the first embodiment shown in FIG. 9 and in the operations of steps S5 to S7. Accordingly, the calibration method according to this modified example includes steps S15 to S17 instead of steps S5 to S7.

Step S15 in this modified example is the same as step S5 in the first embodiment, except that the calibration control unit 101A reads the drive pattern 401 instead of the drive pattern 301 from the storage unit 102.

Step S16 in this modified example is the same as step S6 in the first embodiment, except that the drive motor 34 of the joint portion to be calibrated is driven based on the operation command value $u_m$ based on the drive pattern 401 shown in FIG. 16.

Accordingly, the measured tension differs depending on the maximum value of the drive pattern 401 and the magnitude of the load S varies in the cycles.

In step S17 of this modified example, the calibration control unit 101A selects a combination of the drive pattern and the load S in which measurement accuracy can be considered to be excellent by comparing the maximum value of the drive pattern 401 with the magnitude of the measured load S.

This determination criterion is studied for each joint portion 22 when preparing the control parameter determination information in advance and is stored in the control parameter determination information which is used in this modified example.

For example, the load S may be greatly changed depending on the magnitude of the load condition index $\phi$ in a certain joint portion. For example, in a case in which the load S can be accurately measured when the maximum value of the operation command value $u_m$ is $u_b$ at $\phi=180$ (°) and a case in which the actual load condition at the time of measurement is, for example, $\phi=0$ (°), the load S may be excessively small and the measurement accuracy may be lowered.

In this case, when the driving is performed using the drive pattern 401, the load S calculated from the measurement result of the patterns 401a and 401b is excessively small. On the contrary, the measurement accuracy of the load S calculated from the measurement result of the pattern 401c is excellent.

Then, the calibration control unit 101A determines the control compensation coefficient P with reference to the same control parameter determination information as in the first embodiment using the selected load S, except that the control parameter determination information is prepared based on the maximum value of the operation command value of the cycle corresponding to the measurement.

This is the end of step S17 in this modified example.

According to this modified example, a plurality of patterns having different maximum values such as the drive pattern 401 are provided. Accordingly, even when the load condition at the time of measurement is excessively light or excessively heavy, a proper load S can be calculated by one time of measurement.

In this modified example, the plurality of patterns 401a, 401b, and 401c may be set to appropriate patterns depending on the types of the joint portions 22 of the medical device 20. In this case, in the first embodiment, it is possible to save a labor of switching the drive pattern depending on the type of the joint portion 22 to be calibrated by the calibration control unit 101A.

For example, when $u_c=u_1$ and $u_a=u_2$ are set, the drive pattern 401 includes patterns 401c and 401a suitable for the joint portions 22A and 22B in the first embodiment.

Second Modified Example

A method of calibrating a manipulator according to a second modified example of the first embodiment will be described below.

Figure 17:
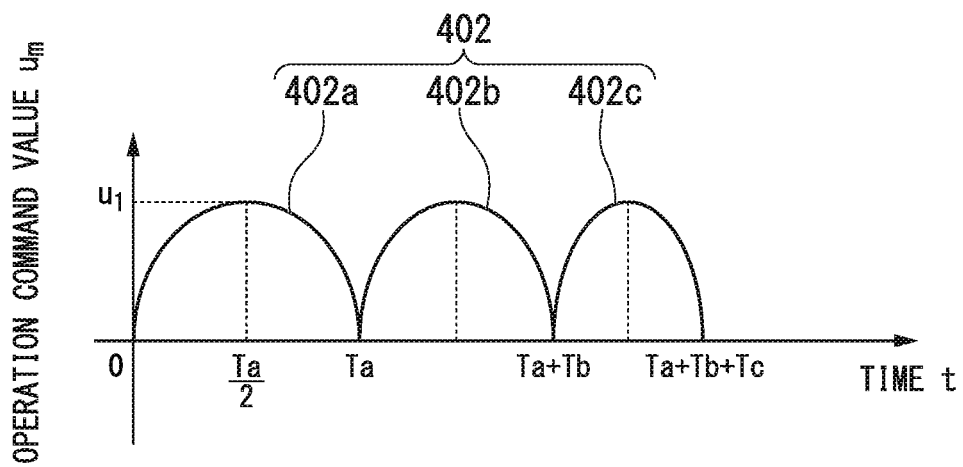
FIG. 17 is a schematic graph showing an example of a drive pattern which is used in a method of calibrating a manipulator according to a second modified example of the first embodiment of the present invention.

FIG. 17 is a schematic graph showing an example of a drive pattern which is used in the method of calibrating a manipulator according to the second modified example of the first embodiment of the present invention. The horizontal axis represents the time t and the vertical axis represents the operation command value $u_m$.

The method of calibrating a manipulator according to this modified example is a modified example in which the drive pattern in the first embodiment is changed and is a method which can be applied to calibration of the medical device 20 in the manipulator system 1 according to the first embodiment.

In this modified example, the control unit 5 includes a calibration control unit 101B (control unit) instead of the calibration control unit 101 in the first embodiment as shown in FIG. 6.

As shown in FIG. 17, the storage unit 102 stores a plurality of patterns in which the cycle of the mountain-shaped pattern in the drive pattern 301 in the first embodiment is changed.

For example, a drive pattern 402 shown in FIG. 17 includes patterns 402a, 402b, and 402c in which the cycle T is changed in a descending order such as $T_a$, $T_b$, and $T_c$ in the same mountain-shaped pattern as the drive pattern 301.

The calibration method according to this modified example using the drive pattern 402 will be described below with a focus on a difference from the first embodiment.

The calibration method according to this modified example is different from the calibration method according to the first embodiment in that the operation of the calibration control unit 101 is performed by the calibration control unit 101B in the flow of the first embodiment shown in FIG. 9 and in the operations of steps S5 to S7. Accordingly, the calibration method according to this modified example includes steps S25 to S27 instead of steps S5 to S7.

Step S25 in this modified example is the same as step S5 in the first embodiment, except that the calibration control unit 101B reads the drive pattern 402 instead of the drive pattern 301 from the storage unit 102.

Step S26 in this modified example is the same as step S6 in the first embodiment, except that the drive motor 34 of the joint portion to be calibrated is driven based on the operation command value $u_m$ based on the drive pattern 401 shown in FIG. 17.

Accordingly, the measured tension differs depending on the cycle of the drive pattern 402 and the magnitude of the load S varies in the cycles.

The reason is considered as a variation of the load due to an influence of a driving velocity.

In step S27 of this modified example, the calibration control unit 101B selects a combination of the drive pattern and the load S in which measurement accuracy can be considered to be excellent by comparing the cycle of the drive pattern 402 with the magnitude of the measured load S.

This determination criterion is studied for each joint portion 22 when preparing the control parameter determination information in advance and is stored in the control parameter determination information which is used in this modified example.

For example, when the cycle of the drive pattern extends, the load S may be excessively small depending on a certain joint portion and the measurement accuracy may be lowered.

In this case, when the driving is performed using the drive pattern 402, the load S calculated from the measurement result of the patterns 402a and 402b is excessively small. On the contrary, the measurement accuracy of the load S calculated from the measurement result of the pattern 402c is excellent.

Then, the calibration control unit 101B determines the control compensation coefficient P with reference to the same control parameter determination information as in the first embodiment using the selected load S, except that the control parameter determination information is prepared based on the maximum value of the operation command value of the cycle corresponding to the measurement.

This is the end of step S27 in this modified example.

According to this modified example, a plurality of patterns having different cycles such as the drive pattern 401 are provided. Accordingly, even when the cycle of the drive pattern at the time of measurement is excessively long or excessively short, a proper load S can be calculated by one time of measurement.

In this modified example, similarly to the first modified example, the plurality of patterns 402a, 402b, and 402c may be set to appropriate patterns depending on the types of the joint portions 22 of the medical device 20. In this case, in the first embodiment, it is possible to save a labor of switching the drive pattern depending on the type of the joint portion 22 to be calibrated by the calibration control unit 101B.

Third Modified Example

A method of calibrating a manipulator according to a third modified example of the first embodiment will be described below.

Figure 18A:
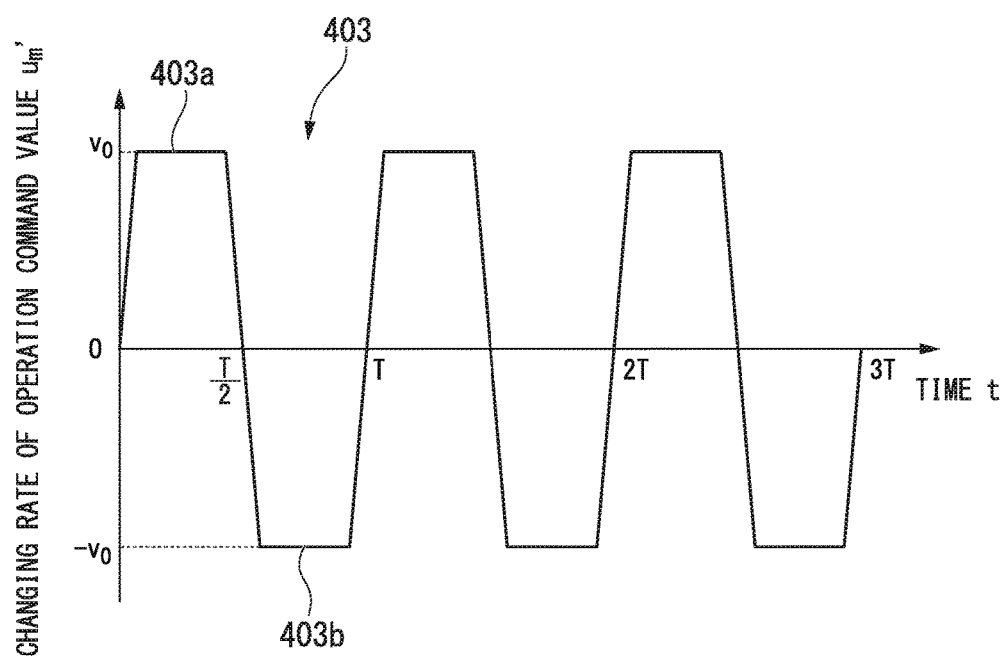
FIG. 18A is a schematic graph showing an example of a drive pattern which is used in a method of calibrating a manipulator according to a third modified example of the first embodiment of the present invention.
Figure 18B:
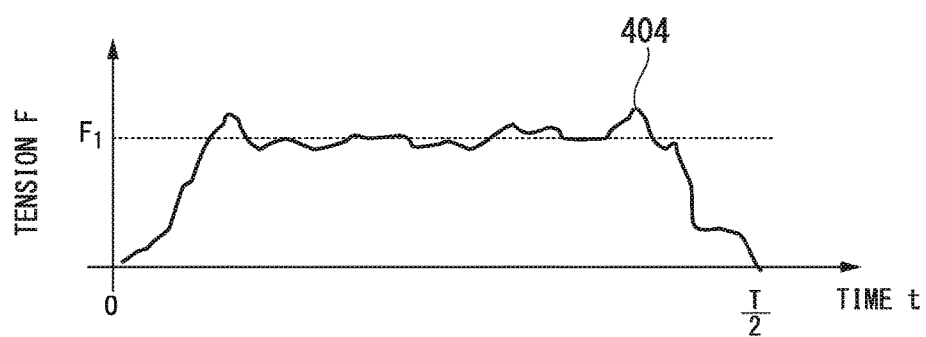
FIG. 18B is a graph showing a measurement example of a tension which is used in the method of calibrating the manipulator according to the third modified example of the first embodiment of the present invention.

FIG. 18A is a schematic graph showing an example of a velocity diagram of a drive pattern which is used in the method of calibrating a manipulator according to the third modified example of the first embodiment of the present invention. The horizontal axis represents the time t and the vertical axis represents a changing rate $u_m'$ of the operation command value. FIG. 18B is a graph showing a measurement example of a tension. The horizontal axis represents the time t and the vertical axis represents the tension F.

The method of calibrating a manipulator according to this modified example is a modified example in which the drive pattern and the load-measuring method in the first embodiment are changed and is a method which can be applied to calibration of the medical device 20 in the manipulator system 1 according to the first embodiment.

In this modified example, the control unit 5 includes a calibration control unit 101C (control unit) instead of the calibration control unit 101 in the first embodiment as shown in FIG. 6.

The storage unit 102 stores a drive pattern having the same velocity diagram as shown in FIG. 18A. The drive pattern is not particularly shown, but is a mountain-shaped repetitive pattern which is obtained by time-integrating the graph of FIG. 18A.

A changing rate pattern 403 indicating the changing rate $u_m'$ of the operation command value $u_m$ is a repetitive pattern of a rectangular wave shape with a cycle T and a half amplitude $V_0$. The number of cycles is not particularly limited, but is, for example, three in FIG. 18A.

The changing rate pattern 403 includes constant-velocity driving parts 403a and 403b in which a velocity is $V_0$ for each half cycle and driving is performed at a constant velocity.

In the constant-velocity driving parts 403a and 403b, the tension F generated in the driving wire 24 is equilibrium with the coulomb frictional force $f_d$ which is the load of the driving wire 24. Accordingly, the measured value of the tension F is equal to the value of $f_d$ as the load.

Since the pulley radius $r_p$ and the spring stiffness k of the driving wire 24 in Equation (6) are constants, the compensation value up can be determined based on Equation (6) by calculating the values in advance.

Accordingly, the control parameter determination information in this modified example includes at least the values of the pulley radius $r_p$ and the spring stiffness k of the driving wire 24 in each joint portion 22.

The spring stiffness k of the driving wire 24 is calculated in advance by measurement or the like.

The calibration method according to this modified example will be described below with a focus on a difference from the first embodiment.

The calibration method according to this modified example is different from the calibration method according to the first embodiment in that the operation of the calibration control unit 101 is performed by the calibration control unit 101C in the flow of the first embodiment shown in FIG. 9 and in the operations of steps S5 to S7. Accordingly, the calibration method according to this modified example includes steps S35 to S37 instead of steps S5 to S7.

Step S35 in this modified example is the same as step S5 in the first embodiment, except that the calibration control unit 101C reads a drive pattern based on the changing rate pattern 403 instead of the drive pattern 301 from the storage unit 102.

According to Step S36 in this modified example, the drive motor 34 of the joint portion to be calibrated is driven based on the operation command value $u_m$ based on the changing rate pattern 403 shown in FIG. 18A.

The tension F which is measured at this time is a substantially constant tension corresponding to the constant-velocity driving part 403a as indicated by a curve 404 as the measurement example of a first half cycle in FIG. 18B. Therefore, the calibration control unit 101C acquiring such tension information averages the measured values corresponding to the constant-velocity driving part 403a to calculate the tension FI. Similarly, the tension is calculated from the measured values of the constant-velocity driving parts 403a and 403b in other cycles. The calibration control unit 101c calculates the representative value $F_d$ of the tensions and sets $f_d = F_d$.

For example, an average value can be employed as the representative value of the measured values of the tension F.

This is the end of step S36 in this modified example.

Then, step S37 in this modified example is performed. This step is a step of determining the control parameter corresponding to the load with reference to the control parameter determination information in this modified example.

The calibration control unit 101C acquires $r_p$ and k of the joint portion 22 to be calibrated with reference to $f_d$ calculated in step S36 and the control parameter determination information in this modified example stored in the storage unit 102 and substitutes the acquired values for Equation (9) to determine the control compensation coefficient P. This is the end of step S37.

$$P = \frac{1}{r_p} \cdot \frac{f_d}{k} \quad (9)$$

According to this modified example, the tension $F_{ave}$ when the drive motor 34 is driven at a constant velocity is measured to calculate $f_d$ as the load. Accordingly, since the $r_p$ and k for each joint portion 22 only have to be stored as the control parameter determination information, it is possible to simplify the control parameter determination information.

Fourth Modified Example

A method of calibrating a manipulator according to a fourth modified example of the first embodiment will be described below.

Figure 19A:
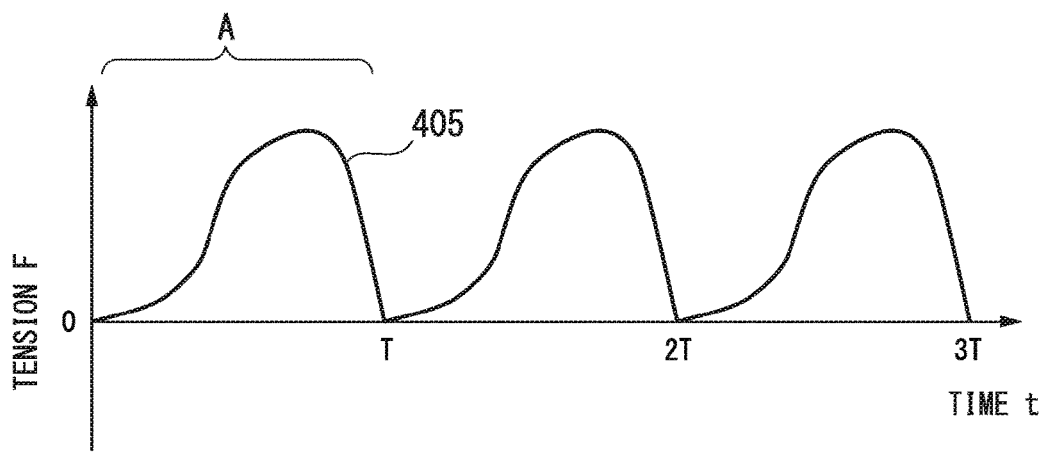
FIG. 19A is a schematic graph showing a measurement example of a load in a method of calibrating a manipulator according to a fourth modified example of the first embodiment of the present invention.
Figure 19B:
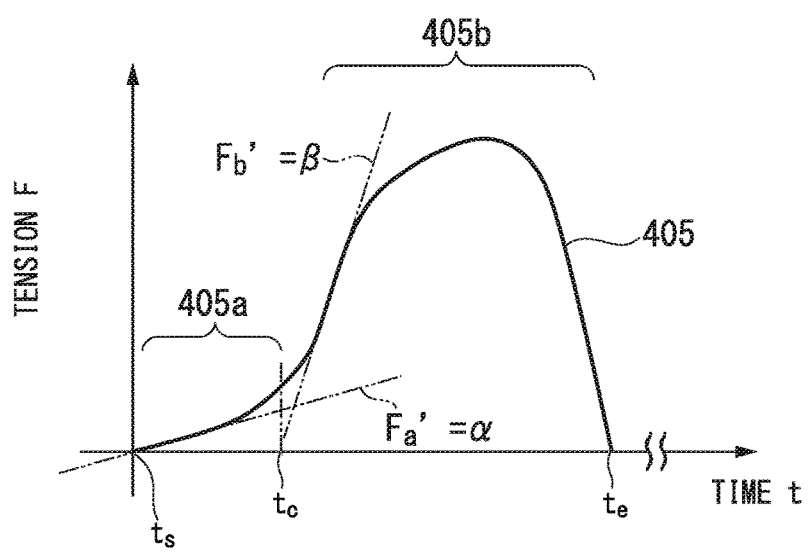
FIG. 19B is a partially-enlarged view of the schematic graph showing a measurement example of a load in the method of calibrating the manipulator according to the fourth modified example of the first embodiment of the present invention.

FIG. 19A is a schematic graph showing a measurement example of a load in the method of calibrating a manipulator according to the fourth modified example of the first embodiment of the present invention. The horizontal axis represents the time t and the vertical axis represents the tension F. FIG. 19B is a partially-enlarged value of FIG. 19A.

The method of calibrating a manipulator according to this modified example is a modified example in which the load-measuring method in the first embodiment is changed and is a method which can be applied to calibration of the medical device 20 in the manipulator system 1 according to the first embodiment.

In this modified example, the drive motor 34 is driven based on the same drive pattern 301 as in the first embodiment and the tension F at that time is measured. However, in this modified example, a degree of looseness generated in the driving wire 24 is estimated from the measurement result of the tension F and the control compensation coefficient P for cancelling the degree of looseness is set.

Accordingly, in this modified example, the control unit 5 includes a calibration control unit 101D (control unit) instead of the calibration control unit 101 in the first embodiment as shown in FIG. 6.

The calibration method according to this modified example will be described below with a focus on a difference from the first embodiment.

The calibration method according to this modified example is different from the calibration method according to the first embodiment in that the operation of the calibration control unit 101 is performed by the calibration control unit 101D in the flow of the first embodiment shown in FIG. 9 and in the operations of steps S6 and S7. Accordingly, the calibration method according to this modified example includes steps S46 and S47 instead of steps S6 and S7.

Step S46 in this modified example is different from step S6 in the first embodiment, in only the load-measuring method.

Accordingly, first, similarly to the first embodiment, a tension is measured by the tension-measuring unit 35 while driving the drive motor 34 for driving the joint portion 22 to be calibrated.

Accordingly, for example, the measurement result of the tension F as indicated by a curve 405 in FIG. 19A is acquired.

The change of the curve 405 in a cycle T is substantially constant. As shown in FIG. 19B, each curve is divided into a slow area 405a in which the change of the tension F is slow and a fast area 405b in which the tension is changed in the same mountain shape as the drive pattern.

In this way, the reason why the slow area 405a appears is that the driving wire 24 is loosened and a load for increasing the tension F is not generated much until the looseness is cancelled.

This looseness is generated by a change in the path length depending on the curved state of the tubular portion 23. That is, as shown in FIG. 5, the driving wire 24 in which the path length is relatively shortened is pushed into the body portion 31 from the sheath 27 and is loosened between the rack 33A and the sheath 27.

Then, in step S47 in this modified example, first, the degree of looseness of the driving wire 24 is estimated from the measurement result of the tension F in step S46.

Specifically, the calibration control unit 101D acquires a time $t_c$ of a boundary between the slow area 405a and the fast area 405b from the magnitude and the changing rate of the tension F in the curve 405 as shown in FIG. 19B.

For example, using the fact that the changing rate $F_a'$ of the tension F is substantially constant as a in the slow area 405a and the changing rate $F_b'$ of the tension F in the fast area 405b adjacent thereto is substantially constant as $\beta$ (where $|\beta|>|\alpha|$), the time $t_c$ at which the changing rate $F_c'$ while the changing rate F' is being changed from $\alpha$ to $\beta$ becomes, for example, $F_c'=(\alpha+\beta)/2$ is calculated. The time may be calculated as a time at a crossing point of both straight lines indicating the tensions F of the slow area 405a and the fast area 405b of which the respective slopes are $F_a'=\alpha$ and $F_b'=\beta$.

When the time $t_c$ is calculated, the calibration control unit 101D calculates a degree of drive $L_1$ of the driving wire 24 which should be pulled by the drive motor 34 from time $t_s$ to time $t_c$ based on the drive pattern.

The calibration control unit 101D similarly calculates degrees of drive $L_2$ and $L_3$ from the measurement results of other cycles, calculates the representative value L thereof, and determines the control compensation coefficient P to be P=L. For example, an average value of the degrees of drive $L_1$, $L_2$, and $L_3$ can be employed as the representative value L.

For example, a value of $L_2$ or subsequent thereto other than the degree of drive $L_1$ may be used as the representative value L.

This is the end of step S47 in this modified example.

In this modified example, since the control compensation coefficient P is set based on the measured value of the tension F, the control parameter is set without particular reference to the control parameter determination information in the control parameter-setting step.

According to this modified example, even when the driving wire 24 is loosened by a load which is applied to the driving wire 24 due to curving of the tubular portion 23 in use, it is possible to perform calibration of estimating the degree of looseness and setting the control parameter. Accordingly, even when looseness occurs, it is possible to accurately drive the joint portion 22.

Fifth Modified Example

A method of calibrating a manipulator according to a fifth modified example of the first embodiment will be described below.

Figure 20:
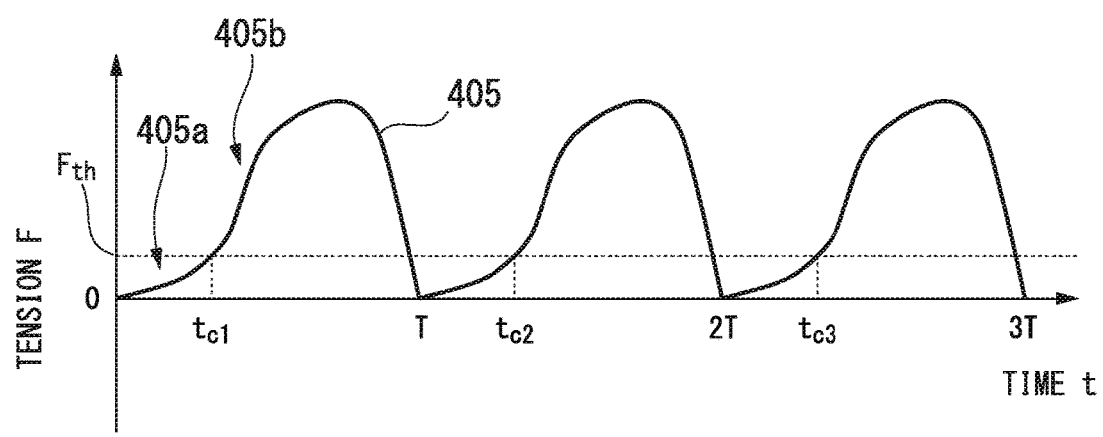
FIG. 20 is a schematic graph showing a method of estimating a degree of looseness of a driving wire in a method of calibrating a manipulator according to a fifth modified example of the first embodiment of the present invention.

FIG. 20 is a graph showing a method of estimating a degree of looseness of a driving wire in the method of calibrating a manipulator according to the fifth modified example of the first embodiment of the present invention. The horizontal axis represents the time t and the vertical axis represents the tension F.

The method of calibrating a manipulator according to this modified example is a modified example of the looseness estimating method in step S7 in the fourth modified example and is a method which can be applied to calibration of the medical device 20 in the manipulator system 1 according to the first embodiment.

In this modified example, the control unit 5 includes a calibration control unit 101E (control unit) instead of the calibration control unit 101D in the fourth modified example as shown in FIG. 6.

The calibration method according to this modified example will be described below with a focus on a difference from the fourth modified example.

The calibration method according to this modified example is different from the calibration method according to the fourth modified example in that the operation of the calibration control unit 101D in the flow of the fourth modified example shown in FIG. 9 is performed by the calibration control unit 101E and in the operation of step S37. Accordingly, the calibration method according to this modified example includes step S57 instead of step S47.

In step S57 in this modified example, the calibration control unit 101E estimates the degree of looseness of the driving wire 24 from the measurement result of the tension F in step S46 which is performed in the same way as in the fourth modified example. In this modified example, using the fact that the changing rate of the tension F in the slow area 405a is small and the absolute value of the tension F is also small, times $t_i$, $t_{c2}$, and $t_{c3}$ at which the tension F becomes greater than a predetermined threshold value $F_{th}$ as shown in FIG. 20 are calculated.

The threshold value $F_{th}$ is control parameter determination information in this modified example, and is prepared for each drive pattern 301 and each joint portion 22 and is stored in advance in the storage unit 102.

When the times $t_{c1}$, $t_{c2}$, and $t_{c3}$ are calculated, the calibration control unit 101E calculates corresponding degrees of drive $L_1$, $L_2$, and $L_3$ similarly to the fourth modified example, calculates the representative value L thereof, and determines the control compensation coefficient P to be P=L. For example, average value of the degrees of drive $L_1$, $L_2$, and $L_3$ can be employed as the representative value L.

This is the end of step S57 in this modified example.

This modified example is different from the fourth modified example, in only the method of estimating a degree of looseness. Accordingly, similarly to the fourth modified example, even when looseness occurs, it is possible to accurately drive the joint portion 22.

Second Embodiment

A manipulator system according to a second embodiment of the present invention will be described below.

Figure 21:
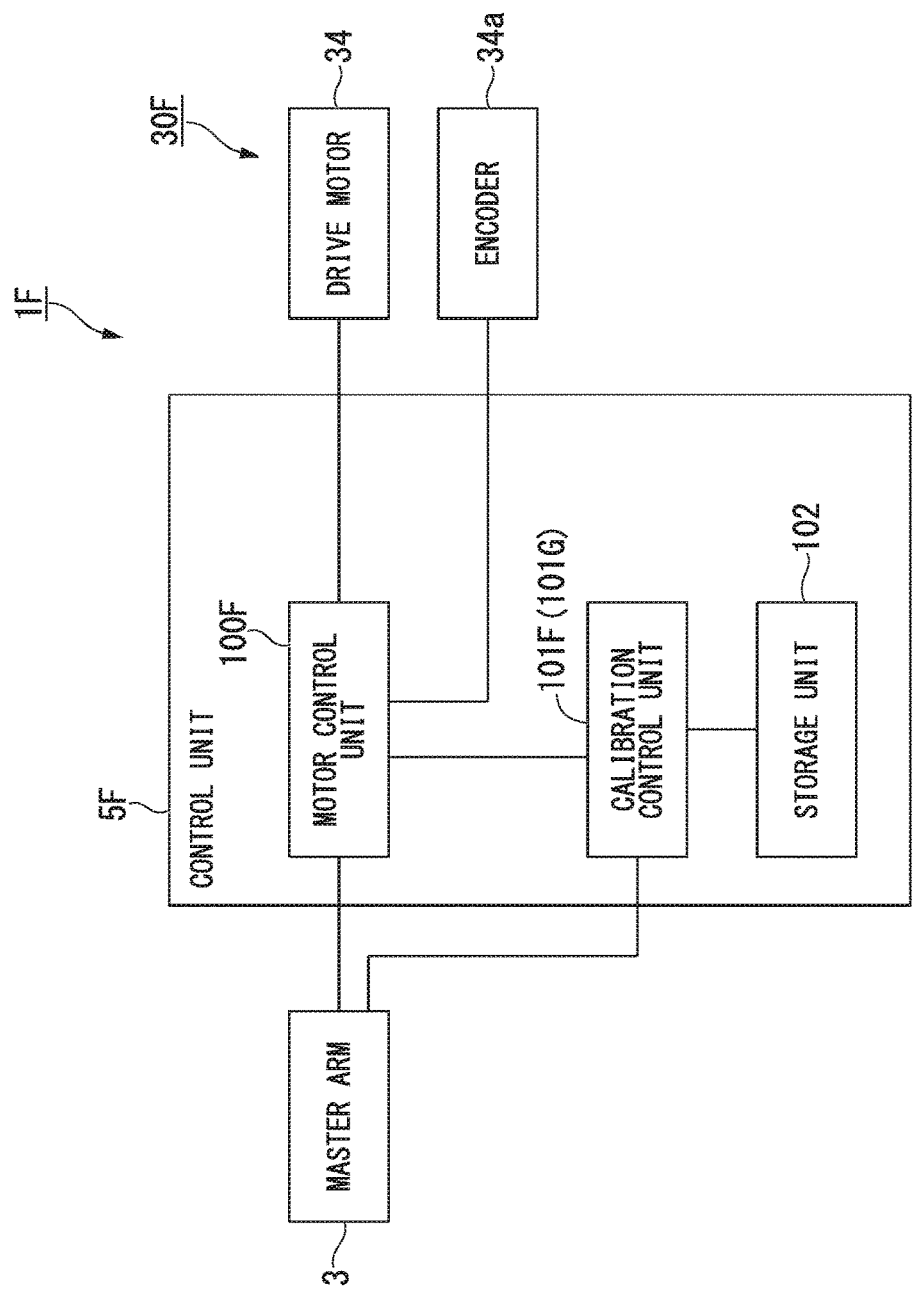
FIG. 21 is a functional block diagram showing a functional configuration of a control unit of a manipulator according to a second embodiment of the present invention.

FIG. 21 is a functional block diagram showing a functional configuration of a control unit of a manipulator according to the second embodiment of the present invention.

As shown in FIG. 1, a manipulator system 1F according to this embodiment includes a medical device 20F and a control unit 5F instead of the medical device 20 and the control unit 5 of the manipulator system 1 according to the first embodiment.

The medical device 20F includes a drive unit 30F instead of the drive unit 30 of the medical device 20 according to the first embodiment as shown in FIG. 4.

The second embodiment will be described below with a focus on a difference from the first embodiment.

In the drive unit 30F in this embodiment, the tension-measuring unit 35 of the drive unit 30 in the first embodiment is removed as shown in FIG. 21. Accordingly, the distal end portion of the ball screw 36 which is not shown is coupled directly to the rack 33A.

The control unit 5F according to this embodiment includes a motor control unit 100F (the control unit, the load-measuring unit) and a calibration control unit 101F (the control unit) instead of the motor control unit 100 and the calibration control unit 101 in the first embodiment.

The motor control unit 100F drives the drive motor 34 in accordance with an operation command from the master arm 3 or the like and measures a load applied to the driving wire 24 similarly to the motor control unit 100, and thus can measure a current value of the drive motor 34. Accordingly, the motor control unit 100F also serves as a load-measuring unit.

The calibration control unit 101F is connected to the motor control unit 100F in a communicable manner and serves to calculate a load S based on the current value of the drive motor 34 through the use of the motor control unit 100F.

With this configuration, the medical device 20F, the motor control unit 100F, the calibration control unit 101F, and the storage unit 102 constitute the manipulator according to this embodiment.

The calibration method of the medical device 20F in the manipulator system 1F will be described below with a focus on a difference from the first embodiment.

The manipulator according to this embodiment is different from the manipulator according to the first embodiment in that the tension-measuring unit 35 is used as the load-measuring unit in the first embodiment but the motor control unit 100F that measures the current value of the drive motor 34 is used.

Since the current value of the drive motor 34 is a measured value representing a driving load, the current value corresponds to the tension of the driving wire 24 one to one. Accordingly, measurement of the load in the first embodiment can be replaced with measurement of the current value.

That is, the calibration method according to this embodiment is different from the calibration method according to the first embodiment, only in that the operations of the calibration control unit 101 and the tension-measuring unit 35 in the flow of the first embodiment shown in FIG. 9 are performed by the calibration control unit 101F and the motor control unit 100F.

In step S7 in this embodiment, the control parameter determination information is prepared in advance as a load measured using the current value of the drive motor 34.

This embodiment is different from the first embodiment, only in that the current value of the drive motor 34 is measured as the load in the load-measuring step. Accordingly, the drive motor 34 is rotated based on the calibrating drive pattern in the first embodiment.

All the drive patterns which are used in the modified examples of the first embodiment can be used as the calibrating drive pattern in this embodiment.

This embodiment is different from the first embodiment in only the load-measuring unit. Accordingly, similarly to the first embodiment, even when a load is applied to the driving force transmission member depending on the arrangement in a usable state, it is possible to easily perform calibration for accurately driving the joint portion.

Particularly, in this embodiment, since the load can be measured without providing the tension-measuring unit 35, it is possible to simplify the device configuration.

Sixth Modified Example

A method of calibrating a manipulator according to a modified example (a sixth modified example) of the second embodiment will be described below.

The method of calibrating a manipulator according to this modified example is a modified example in which the drive pattern and the load-measuring method in the first embodiment are changed and is a method which can be applied to calibration of the medical device 20 in the manipulator system 1 according to the first embodiment.

In this modified example, the control unit 5F includes a calibration control unit 101G (control unit) instead of the calibration control unit 101F in the second embodiment as shown in FIG. 21.

The calibration control unit 101G can acquire information of an encoder 34a from the motor control unit 100F and can issue an operation command of a calibrating drive pattern for driving the drive motor 34 in a predetermined direction with a predetermined torque to the motor control unit 100F.

The calibration control unit 101G acquires a degree of rotation of the drive motor 34 (a degree of motor rotation) based on this driving from the motor control unit 100F and sets the degree of rotation as the load.

Accordingly, in this modified example, the encoder 34a constitutes the load-measuring unit.

The calibration method according to this modified example will be described below with a focus on a difference from the first and second embodiments.

The calibration method according to this modified example is different from the calibration method according to the first embodiment in that the operation of the calibration control unit 101 is performed by the calibration control unit 101G in the flow of the first embodiment shown in FIG. 9 and in the operations of steps S5 to S7. Accordingly, the calibration method according to this modified example includes steps S75 to S77 instead of steps S5 to S7.

Step S75 in this modified example is the same as step S5 in the first embodiment, except that the calibration control unit 101G issues an operation command for setting a drive pattern, which is not shown, for driving the drive motor 34 in a predetermined direction with a predetermined torque instead of the drive pattern 301.

Step S76 in this modified example is the same as step S6 in the first embodiment, except that the drive motor 34 is driven in accordance with the operation command for driving the drive motor in a predetermined direction with a predetermined torque set in step S75 and the degree of rotation until the rotation of the drive motor 34 is stopped is acquired as the load.

Then, in step S77 in this modified example, the calibration control unit 101G determines the degree of rotation measured in step S76 as the control compensation coefficient P with reference to the control parameter determination information of this modified example stored in the storage unit 102.

This modified example is different from the second embodiment in only the load-measuring method. Accordingly, similarly to the second embodiment, even when a load is applied to the driving force transmission member depending on the arrangement in a usable state, it is possible to easily perform calibration for accurately driving the joint portion.

Third Embodiment

A manipulator system according to a third embodiment of the present invention will be described below.

Figure 22:
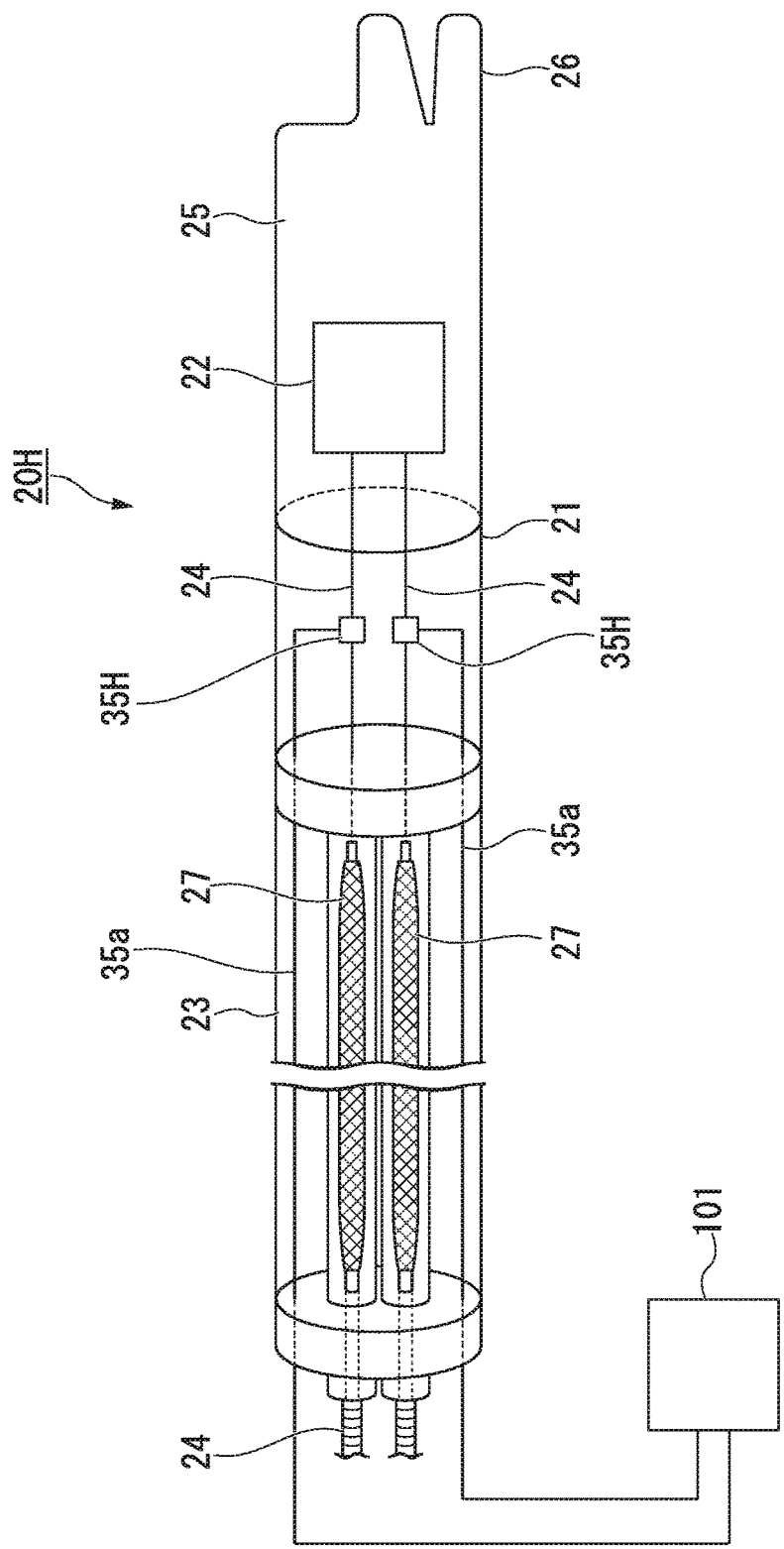
FIG. 22 is a diagram schematically showing a configuration of a manipulator according to a third embodiment of the present invention.

FIG. 22 is a diagram showing a schematic configuration of a manipulator according to the third embodiment of the present invention.

As shown in FIG. 22, a manipulator according to this embodiment includes a medical device 20H instead of the medical device 20 of the manipulator system 1 according to the first embodiment.

The medical device 20H includes a tension-measuring unit 35H (load-measuring unit) instead of the tension-measuring unit 35 of the medical device 20 of the first embodiment. The manipulator according to this embodiment including the medical device 20H can be used for the manipulator system 1 according to the first embodiment.

The third embodiment will be described below with a focus on a difference from the first embodiment.

The tension-measuring unit 35H of this embodiment measures a tension generated in the driving wire 24 and is attached to the driving wire 24 inside the shaft-shaped portion 21. In this embodiment, the tension-measuring unit is disposed in each of the driving wires 24 which are disposed in parallel to drive the joint portions 22 so as to measure a tension in any driving direction.

The configuration of the tension-measuring unit 35H is not particularly limited as long as it can measure a tension. In this embodiment, the tension-measuring unit 35H employs a tension sensor using a strain gauge.

Each tension-measuring unit 35H is connected to the calibration control unit 101 in a communicable manner by a wire 35a which is inserted into the shaft-shaped portion 21 and the tubular portion 23 and extends to the control unit 5 which is not shown.

Accordingly, the calibration control unit 101 can acquire a detection signal of the tension-measuring unit 35H when the joint portions 22 are driven.

With this configuration, the medical device 20H, the motor control unit 100, the calibration control unit 101, the tension-measuring unit 35H, and the storage unit 102 constitute the manipulator according to this embodiment.

In the manipulator according to this embodiment, the tension-measuring unit 35H as the load-measuring unit is disposed in the vicinity of the joint portion 22 in the distal-bending portion 25.

This embodiment is different from the first embodiment in only the arrangement position of the load-measuring unit. Accordingly, similarly to the first embodiment, even when a load is applied to the driving force transmission member depending on the arrangement in a usable state, it is possible to easily perform calibration for accurately driving the joint portion.

Particularly, in this embodiment, since the tension-measuring unit 35H can measure the load at a position close to the joint portion 22, it is possible to perform calibration based on the load condition in the vicinity of the joint portion 22.

In the first embodiment and the like, the calibrating drive pattern is exemplified by a half-pulsating drive pattern, but the drive pattern is not limited to this example.

Figure 23:
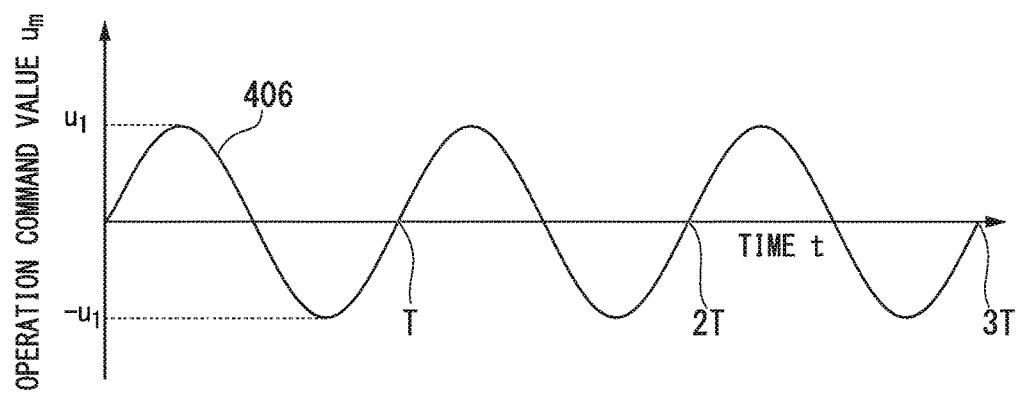
FIG. 23 is a schematic graph showing another example of a drive pattern which can be commonly used in the embodiments and the modified examples of the present invention.

For example, a full-pulsating drive pattern may be used as shown in FIG. 23.

FIG. 23 is a schematic graph showing another example of the drive pattern which can be commonly used in the embodiments and the modified examples of the present invention. The horizontal axis represents the time t and the vertical axis presents the operation command value $u_m$.

A drive pattern 406 shown in FIG. 23 is a sinusoidal drive pattern with a half amplitude $u_1$ and a cycle T.

In the embodiments and the modified examples, the grasping portion 26 which is a grasping forceps is used as the end effector of the manipulator, but the end effector is not limited to the grasping portion 26 and can employ an appropriate device part such as a high-frequency treatment tool, a local injection needle, a separating forceps, or a suction depending on the manipulation types. The end effector is not limited to a moving mechanism such as the grasping portion 26. For example, an end effector which is merely fixed to a distal end such as the observation unit 15 of the treatment endoscope device 10 may be employed.

In the embodiments and the modified examples, the method of calibrating a manipulator is a method of calibrating a medical manipulator, but the present invention can be similarly applied to a manipulator such as an industrial manipulator other than the medical manipulator.

In the embodiments and the modified examples, the distal-bending portion 25 includes two joint portions 22A and 22B having different bending directions, but the number of joint portions or the degree of freedom thereof may be set appropriately in consideration of details of the manipulation. For example, the number of joint portions may be only one.

The same mechanism as the bending portion 11B in the outer sheath 11 may be used instead of the combination of the joint portion and the tubular portion. That is, when a plurality of joint rings or curving pieces which are the shaft-shaped portion are coupled to a rotating joint which is a bending joint, one or more rotating joints can be initialized as the same way.

In the embodiments and the modified examples, the joint portion-restricting member is constituted by the through-hole portion 12 of the treatment endoscope device 10, but the joint portion-restricting member is not limited to the hole portion and may be constituted by an appropriate groove portion or an appropriate locking portion that restricts a joint portion.

The restricting of the joint portion is not particularly limited as long as the movement thereof in the calibrating operation can be restricted, and may be achieved using a soft member depending on the driving force in the calibrating operation. For example, the treatment tool channel 16 may be used as the joint portion-restricting member.

In addition, an end lifter, a grasping manipulator, or the like which is arranged at a position to be calibrated in the body of a patient Pa or the like along with the manipulator may be used as the joint portion-restricting member.

The joint portion-restricting member may be disposed as a dedicated instrument depending on the use environment of the manipulator.

In the embodiments and the modified examples, the movement of the joint portion is restricted to fix the environmental stiffness in the calibration operation. However, when the environmental stiffness is known, the calibrating operation may be performed without restricting the movement of the joint portion.

For example, when the environmental stiffness of the calibrating operation and the environmental stiffness of the measuring operation for acquiring the control parameter determination information can be matched with each other, the movement of the joint portion may not be restricted.

The joint portion-restricting member is not limited to complete restricting of the movement of the joint portion. For example, the joint portion may be restricted to be movable to a certain extent such that a predetermined load is applied to the joint.

In the embodiments and the modified examples, the manipulator is used in the manipulator system, but the present invention may be used to calibrate the manipulator as a single device.

In the embodiments and the modified examples, the driving force transmission member is a wire, but the driving force transmission member is not limited to the wire. For example, a cable or a flexible rod may be used as the driving force transmission member.

In the embodiments and the modified examples, the driving force transmission member employs, for example, the rack-and-pinion mechanism, but the driving force transmission member may employ an appropriate driving force transmission mechanism which is used in a manipulator.

For example, a driving force transmission mechanism that pulls the driving force transmission member in a rotating direction by winding and rotating the driving force transmission member on a drive pulley to rotate the drive pulley using a drive motor may be employed.

In this case, for example, by coupling the rotating shaft of the drive pulley and the rotating shaft of the drive motor via a detachable joint, the drive motor may be detachably attached.

In the embodiments and the modified examples, the joint portions 22 are individually calibrated one by one, but two or more joint portions 22 may be simultaneously calibrated by appropriately setting the length of the through-hole portion 12.

In the embodiments and the modified examples, the joint portion is a bending joint, but the joint portion is not limited to the bending joint as long as it is a joint portion which is driven by the driving force transmission member. A joint portion such as a rotating joint may be used.

In the first embodiment, Equation (7) is used to calculate the load S. A negative region of a tension may appear as an actual measured waveform, but should not occur in principle when the driving wire is ideally loosened. Accordingly, the negative region may be considered as a measurement error and the load S may be calculated by adding only a positive region of a tension.

All the above-mentioned elements may be appropriately combined or deleted within the technical spirit of the present invention.

For example, a joint portion for driving the grasping portion 26 may be calibrated using the calibration methods according to the embodiments and the modified examples.

While the embodiments and the modified examples of the present invention have been described in detail with reference to the drawings, the specific configuration is not limited to the embodiments but includes a modification in design without departing from the gist of the present invention. The elements in the above-mentioned embodiments may be appropriately combined. The present invention is not limited to the above description but is defined by only the scope of the appended claims.

What is claimed is:

1. A method of calibrating a manipulator including a joint portion, a drive unit that generates a driving force to drive the joint portion, and a driving force transmission member that is inserted into a tubular member and provided to transmit the driving force generated from the drive unit to the joint portion, the method comprising:
    an arrangement step of arranging the manipulator into a treatment tool channel;
    a load-measuring step of issuing an operation command to the drive unit for moving the joint portion based on a predetermined calibrating drive pattern and measuring a load generated in the manipulator at that time; and
    a control parameter-setting step of setting a main-driving control parameter based on the load measured in the load-measuring step to calibrate the manipulator.

2. The method of calibrating a manipulator according to claim 1,
    wherein the predetermined calibrating drive pattern is determined from among a plurality of patterns.

3. The method of calibrating a manipulator according to claim 2,
    wherein the predetermined calibrating drive pattern is determined from among the plurality of patterns depending on a type of the manipulator.

4. The method of calibrating a manipulator according to claim 1,
    wherein the predetermined calibrating drive pattern comprises a drive pattern having a constant-velocity driving part.

5. The method of calibrating a manipulator according to claim 1, further comprising a joint portion-restricting step of restricting movement of the joint portion that is performed before the load-measuring step,
    wherein the load-measuring step is performed in a state in which the movement of the joint portion is restricted.

6. The method of calibrating a manipulator according to claim 1,
    wherein the load-measuring step comprises measuring a tension which is generated in the driving force transmission member as the load.

7. The method of calibrating a manipulator according to claim 6,
    wherein the control parameter-setting step comprises setting the main-driving control parameter based on a value obtained by temporally integrating the tension which is measured as the load.

8. The method of calibrating a manipulator according to claim 6,
    wherein the control parameter-setting step comprises setting the main-driving control parameter based on a variation in a changing rate of the tension which is measured as the load.

9. The method of calibrating a manipulator according to claim 6,
    wherein the control parameter-setting step comprises setting the main-driving control parameter based on a timing at which the tension which is measured as the load becomes greater than a predetermined threshold.

10. The method of calibrating a manipulator according to claim 1,
    wherein the drive unit includes a motor, and
    wherein the load-measuring step comprises measuring a current value of the motor as the load.

11. The method of calibrating a manipulator according to claim 10,
    wherein the load-measuring step uses a drive pattern in which the motor is rotated by a predetermined degree as the predetermined calibrating drive pattern.

12. The method of calibrating a manipulator according to claim 1,
    wherein the drive unit includes a motor, and
    wherein the load-measuring step comprises measuring a degree of motor rotation when the motor is driven with a predetermined torque as the load.

13. The method of calibrating a manipulator according to claim 1,
    wherein the control parameter-setting step comprises setting a control parameter which is determined based on the load and predetermined control parameter determination information as the main-driving control parameter.

14. The method of calibrating a manipulator according to claim 13,
    wherein the predetermined control parameter determination information comprises information of the load which is measured in the same way as in the load-measuring step in a plurality of load conditions, which are formed by curving the tubular member of the manipulator, and information of the control parameter for realizing the operation command of the drive pattern in the plurality of load conditions.

15. A manipulator comprising:
    a joint portion;
    a drive unit configured to generate a driving force for driving the joint portion;
    a driving force transmission member configured to be inserted into a tubular member and to transmit the driving force generated from the drive unit to the joint portion;
    a storage unit configured to store a predetermined calibrating drive pattern;
    a load-measuring unit configured to measure a load generated in the manipulator when the joint portion is driven by the driving force; and
    a control unit configured to perform operation control of the drive unit and setting of a control parameter,
    wherein the control unit is configured to issue an operation command based on the predetermined calibrating drive pattern stored in the storage unit to the drive unit and acquire a value of the load which is measured by the load-measuring unit at that time, and
    wherein the control unit is configured to set a main-driving control parameter based on the load measured by the load-measuring unit.

16. The manipulator according to claim 15,
    wherein the load-measuring unit comprises a tension-measuring unit configured to measure a tension which is generated in the driving force transmission member as the load.

17. The manipulator according to claim 16,
    wherein the drive unit is disposed to be detachable from an insertion portion including the joint portion and the driving force transmission member, and
    wherein the tension-measuring unit is disposed between the driving force transmission member and the drive unit and is detachably fixed to the insertion portion along with the drive unit.

18. The manipulator according to claim 15,
wherein the drive unit comprises a motor and is disposed to be detachable from an insertion portion including the joint portion and the driving force transmission member, and
wherein the load-measuring unit measures a current value of the motor.

19. A manipulator system comprising the manipulator according to claim 15.

20. The manipulator system according to claim 19, further comprising a joint portion-restricting member that restricts movement of the joint portion.

* * * * *